(12) United States Patent
Bates et al.

(10) Patent No.: US 7,297,115 B2
(45) Date of Patent: Nov. 20, 2007

(54) IMMERSIBLE ULTRASOUND PROBE AND CABLE

(75) Inventors: Kenneth N. Bates, Beaverton, OR (US); William McDonough, McMinnville, OR (US); Ronald Schutz, Portland, OR (US); Evan Dudik, Vancouver, WA (US)

(73) Assignee: Black Toe Medical III, Inc., Portland, OR (US)

( * ) Notice: Subject to any disclaimer, the term of this patent is extended or adjusted under 35 U.S.C. 154(b) by 528 days.

(21) Appl. No.: 10/724,382

(22) Filed: Nov. 26, 2003

(65) Prior Publication Data

US 2004/0111029 A1 Jun. 10, 2004

Related U.S. Application Data

(60) Provisional application No. 60/429,614, filed on Nov. 27, 2003.

(51) Int. Cl.
*A61B 8/00* (2006.01)
*H01R 13/52* (2006.01)

(52) U.S. Cl. .................. 600/437; 600/459; 439/271; 439/909

(58) Field of Classification Search ............... 600/437, 600/443, 447, 456–472; 439/271–283, 212–213, 439/445–447, 578, 587–588, 909
See application file for complete search history.

(56) References Cited

U.S. PATENT DOCUMENTS

| | | | |
|---|---|---|---|
| 4,003,621 A | | 1/1977 | Lamp |
| 4,250,894 A | * | 2/1981 | Frei et al. .................. 600/587 |
| 4,407,295 A | * | 10/1983 | Steuer et al. ............... 600/483 |
| 4,545,386 A | * | 10/1985 | Hetz et al. ................. 600/462 |
| 4,671,292 A | | 6/1987 | Matzuk |
| 4,693,529 A | | 9/1987 | Stillie |
| 4,913,656 A | | 4/1990 | Gordon et al. |
| 4,940,413 A | | 7/1990 | Childers et al. |

(Continued)

OTHER PUBLICATIONS

Stanton, Robert E., High Density Pad Grid Array Interconnect System, AMP Journal of Technology, Nov. 3, 1993, 6pgs., vol. 3, U.S.

(Continued)

*Primary Examiner*—Francis J. Jaworski

(57) ABSTRACT

A ultrasound platform is used to generate, process and display ultrasound images using a probe connected via a sterilizable connector. The probe is used to take ultrasound images, and can be a sterilizable finger mounted probe. The sterilizable connector includes a connector housing which has been sealed to prevent moisture from entering it, and a multi-wire cable which is electrically coupled to the probe at a first end and coupled to the connector housing at a second end. The multi-wire cable has its second end sealed with the connector housing to prevent moisture from entering the sealing between the multi-wire cable and the connector housing. A plurality of electrical contacts are formed on at least one surface of the sterilizable connector. A mating connector is used to electrically couple the sterilizable connector to a standard connector for directly connecting to the ultrasound platform. The mating connector has a plurality of mating contacts formed thereon for electrical coupling with the electrical contacts of the sterilizable connector. The sterilizable connector can be separated from the standard connector and the mating connector, such that the probe and the sterilizable connector can be sterilized.

29 Claims, 19 Drawing Sheets

U.S. PATENT DOCUMENTS

| | | | |
|---|---|---|---|
| 4,972,839 A | 11/1990 | Angelsen | |
| 5,026,291 A | 6/1991 | David | |
| 5,088,500 A * | 2/1992 | Wedel et al. | 600/452 |
| 5,123,852 A | 6/1992 | Gillett | |
| 5,152,293 A * | 10/1992 | Vonesh et al. | 600/459 |
| 5,199,881 A | 4/1993 | Oshita et al. | |
| 5,265,329 A | 11/1993 | Jones et al. | |
| 5,284,147 A | 2/1994 | Hanaoka et al. | |
| 5,372,512 A | 12/1994 | Wilson et al. | |
| 5,381,795 A | 1/1995 | Nordgren et al. | |
| 5,385,477 A | 1/1995 | Vaynkof et al. | |
| 5,403,194 A | 4/1995 | Yamazaki | |
| 5,413,107 A * | 5/1995 | Oakley et al. | 600/463 |
| 5,452,717 A * | 9/1995 | Branigan et al. | 600/323 |
| 5,461,482 A | 10/1995 | Wilson et al. | |
| 5,533,904 A | 7/1996 | Nobel et al. | |
| 5,573,409 A | 11/1996 | Shiley et al. | |
| 5,597,982 A | 1/1997 | Hiwada | |
| 5,598,194 A | 1/1997 | Hall et al. | |
| 5,598,846 A | 2/1997 | Peszynski | |
| 5,604,976 A | 2/1997 | Stobie et al. | |
| 5,630,419 A * | 5/1997 | Ranalletta | 600/459 |
| 5,782,645 A | 7/1998 | Stobie et al. | |
| 5,795,299 A | 8/1998 | Eaton et al. | |
| 5,805,424 A | 9/1998 | Purinton | |
| 5,805,425 A | 9/1998 | Peterson | |
| 5,805,426 A | 9/1998 | Merritt et al. | |
| 5,818,700 A | 10/1998 | Purinton | |
| 5,846,097 A | 12/1998 | Marian, Jr. | |
| 5,904,580 A | 5/1999 | Kuzel et al. | |
| 5,913,688 A | 6/1999 | Marian, Jr. | |
| 6,024,579 A | 2/2000 | Bennett | |
| 6,029,530 A | 2/2000 | Patton et al. | |
| 6,052,286 A | 4/2000 | Worthen et al. | |
| 6,106,305 A | 8/2000 | Kozel et al. | |
| 6,123,551 A | 9/2000 | Westfall | |
| 6,309,358 B1 * | 10/2001 | Okubo | 600/466 |
| 6,350,122 B1 | 2/2002 | Glatts, III | |
| 6,350,132 B1 | 2/2002 | Glatts, III | |
| 6,358,064 B2 | 3/2002 | Szaley et al. | |
| 6,671,531 B2 * | 12/2003 | Al-Ali et al. | 600/344 |
| 6,746,402 B2 | 6/2004 | Ustuner | |
| 2004/0225217 A1 * | 11/2004 | Voegele et al. | 600/439 |
| 2005/0085731 A1 | 4/2005 | Miller et al. | |

OTHER PUBLICATIONS

International Search Report of PCT/US03/38182, dated Oct. 25, 2005.

* cited by examiner

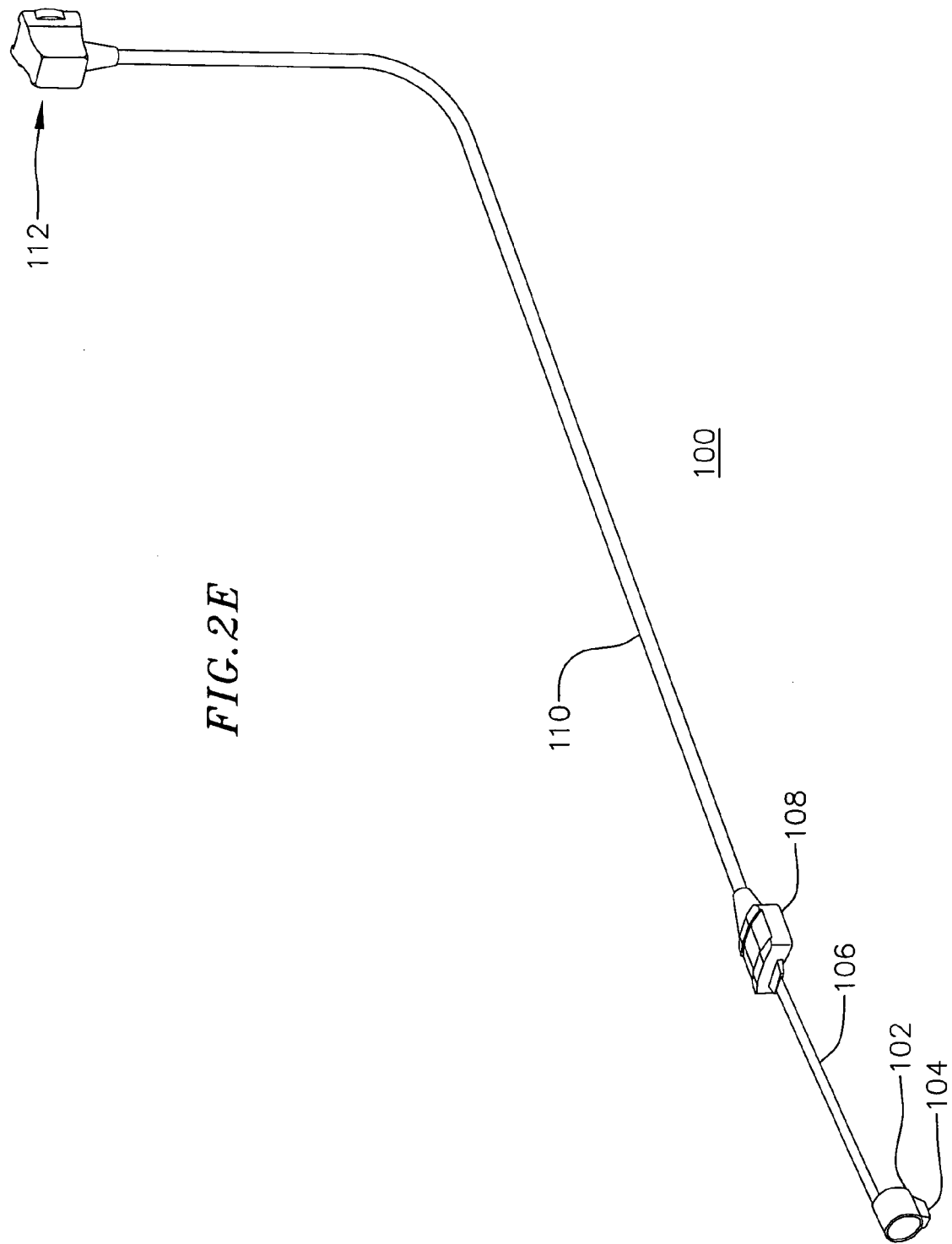

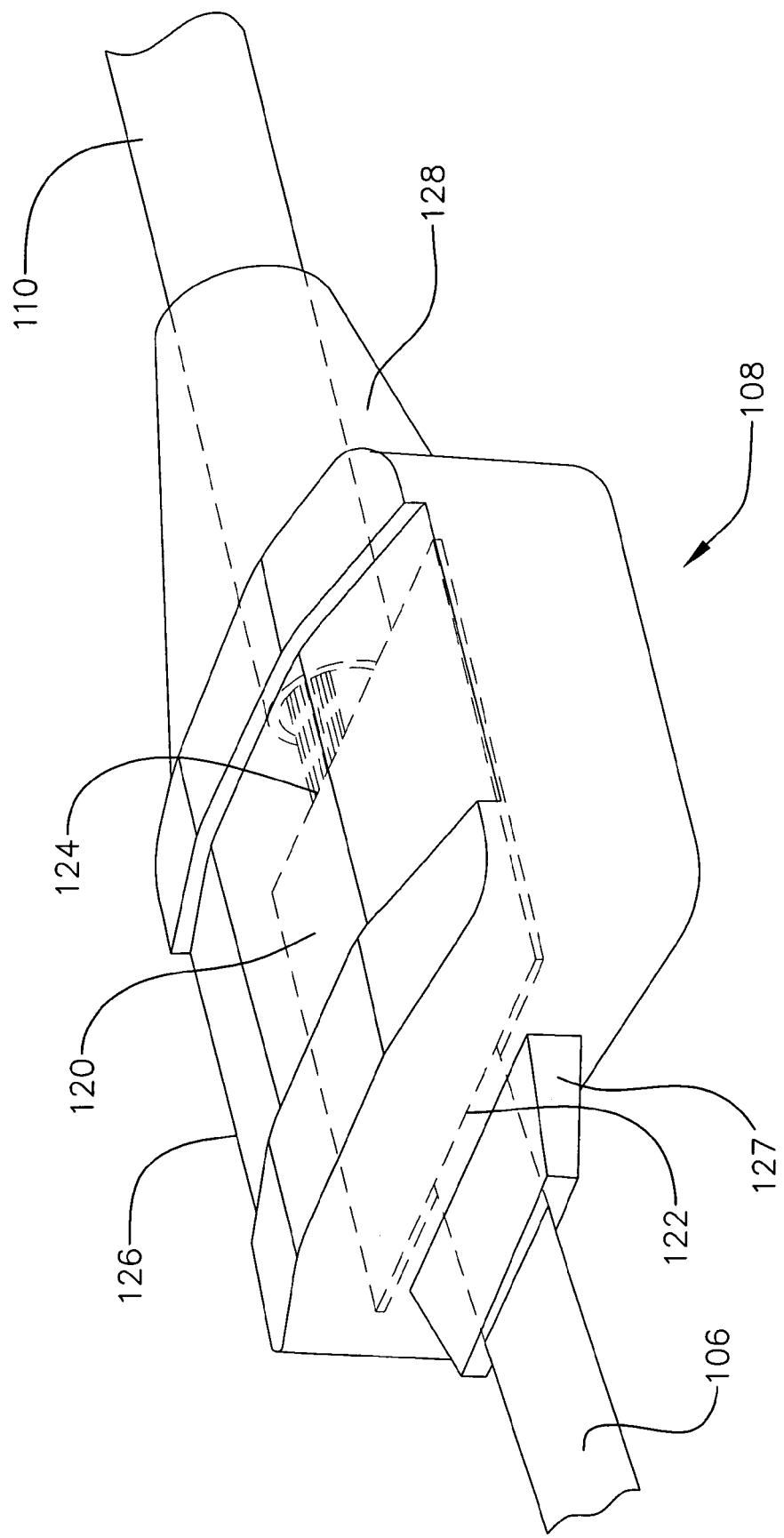

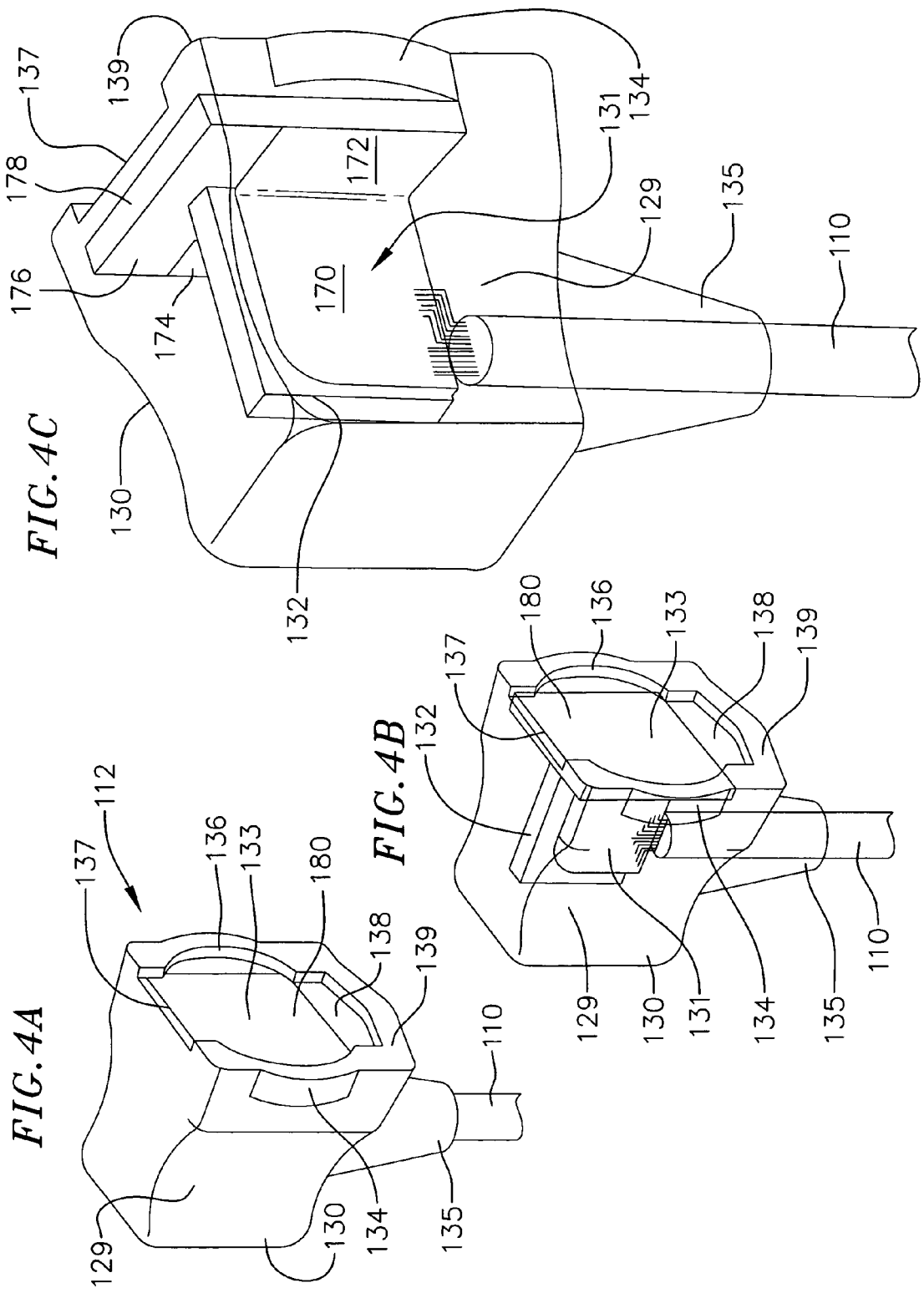

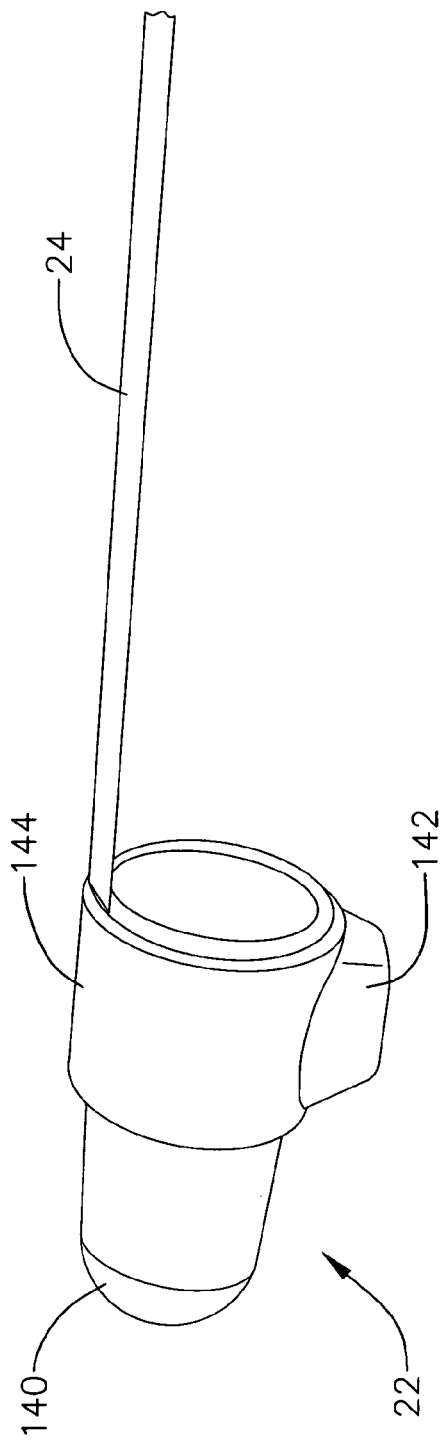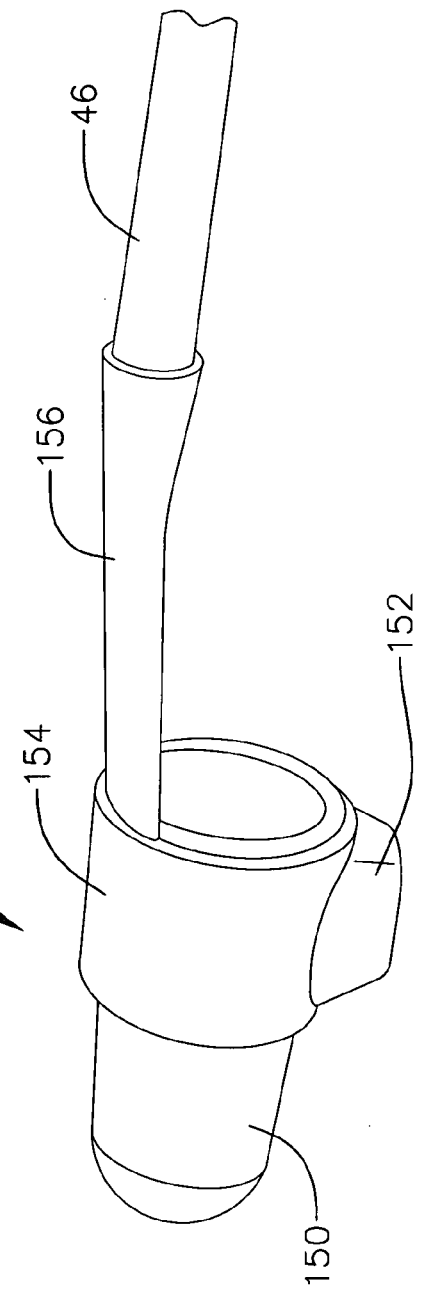

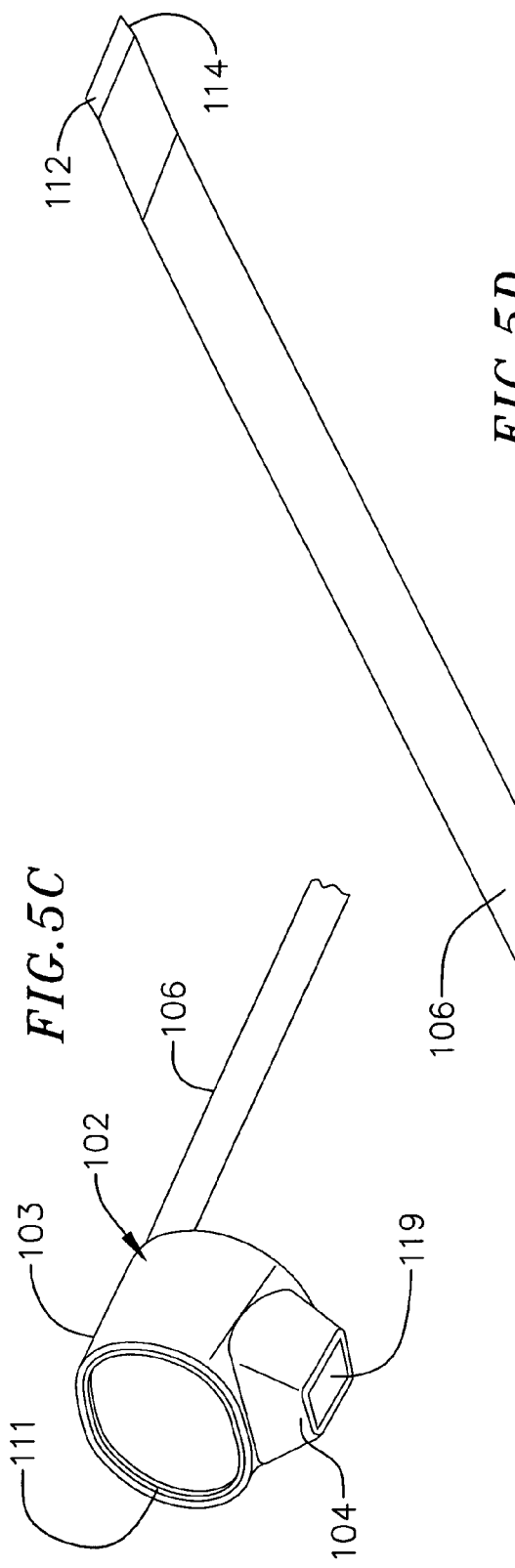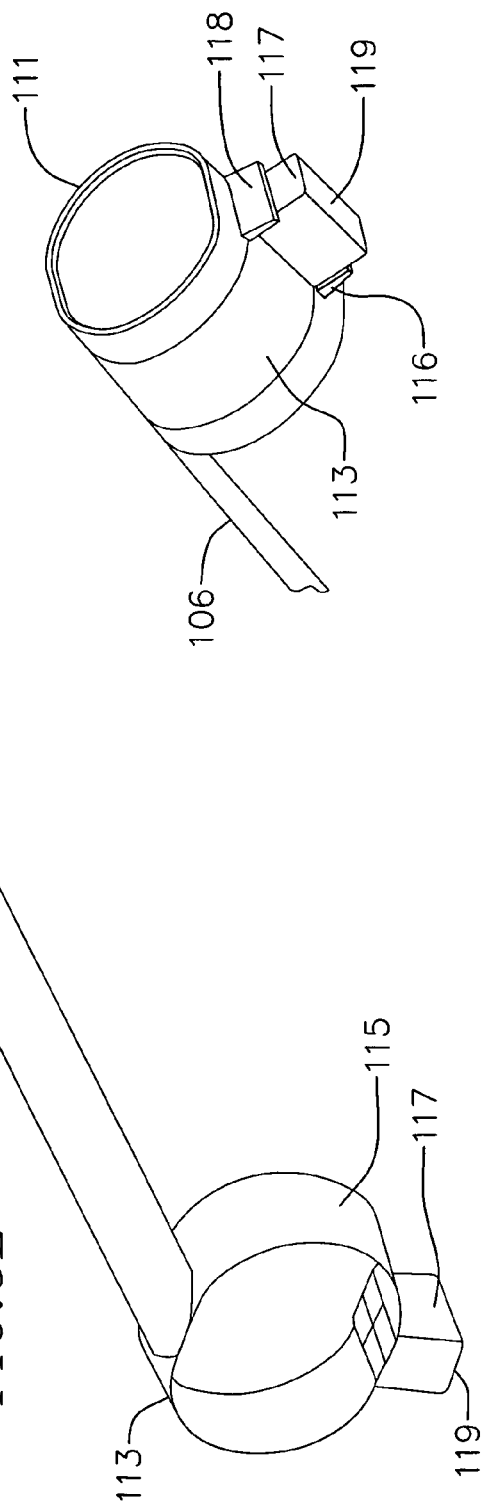

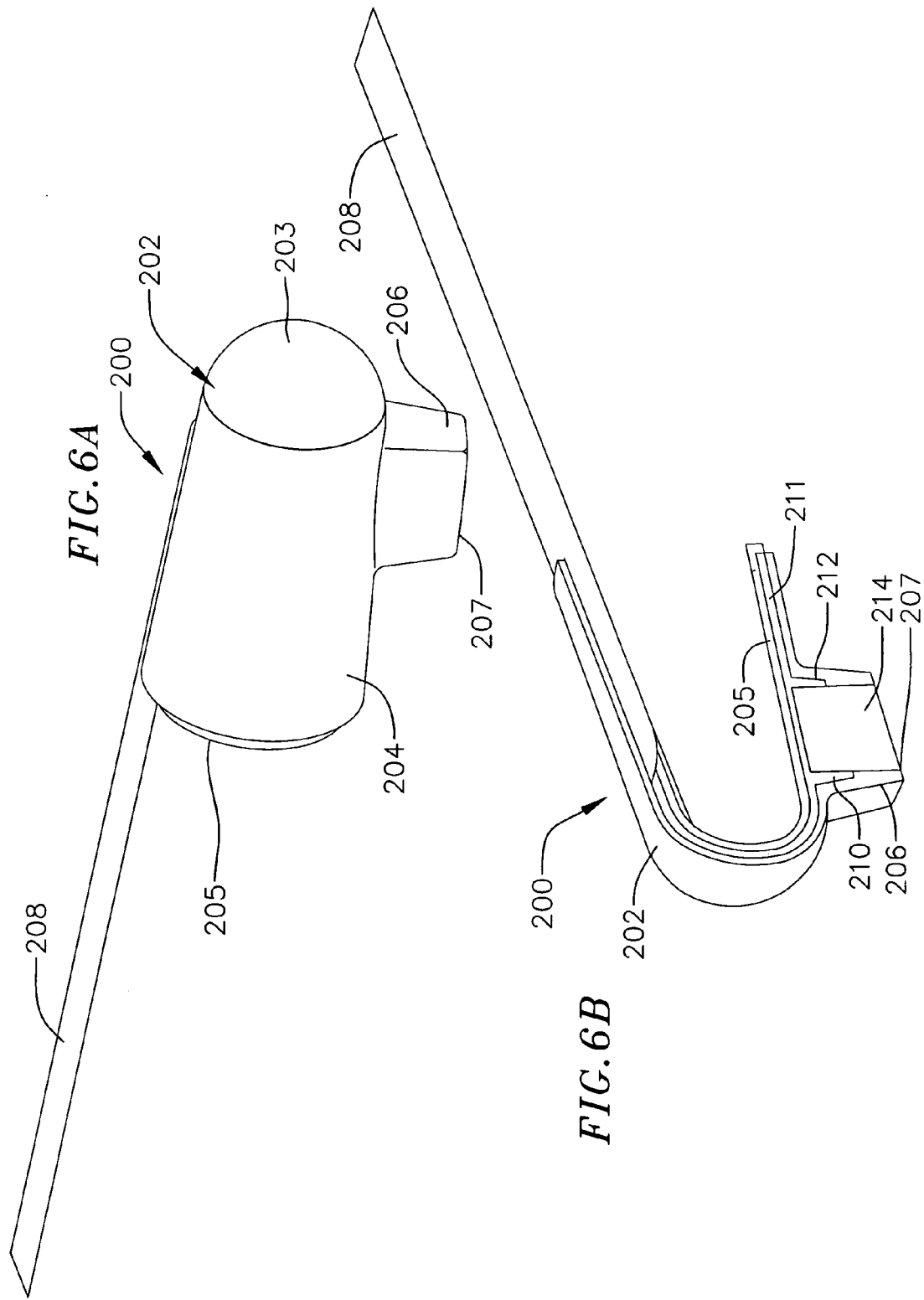

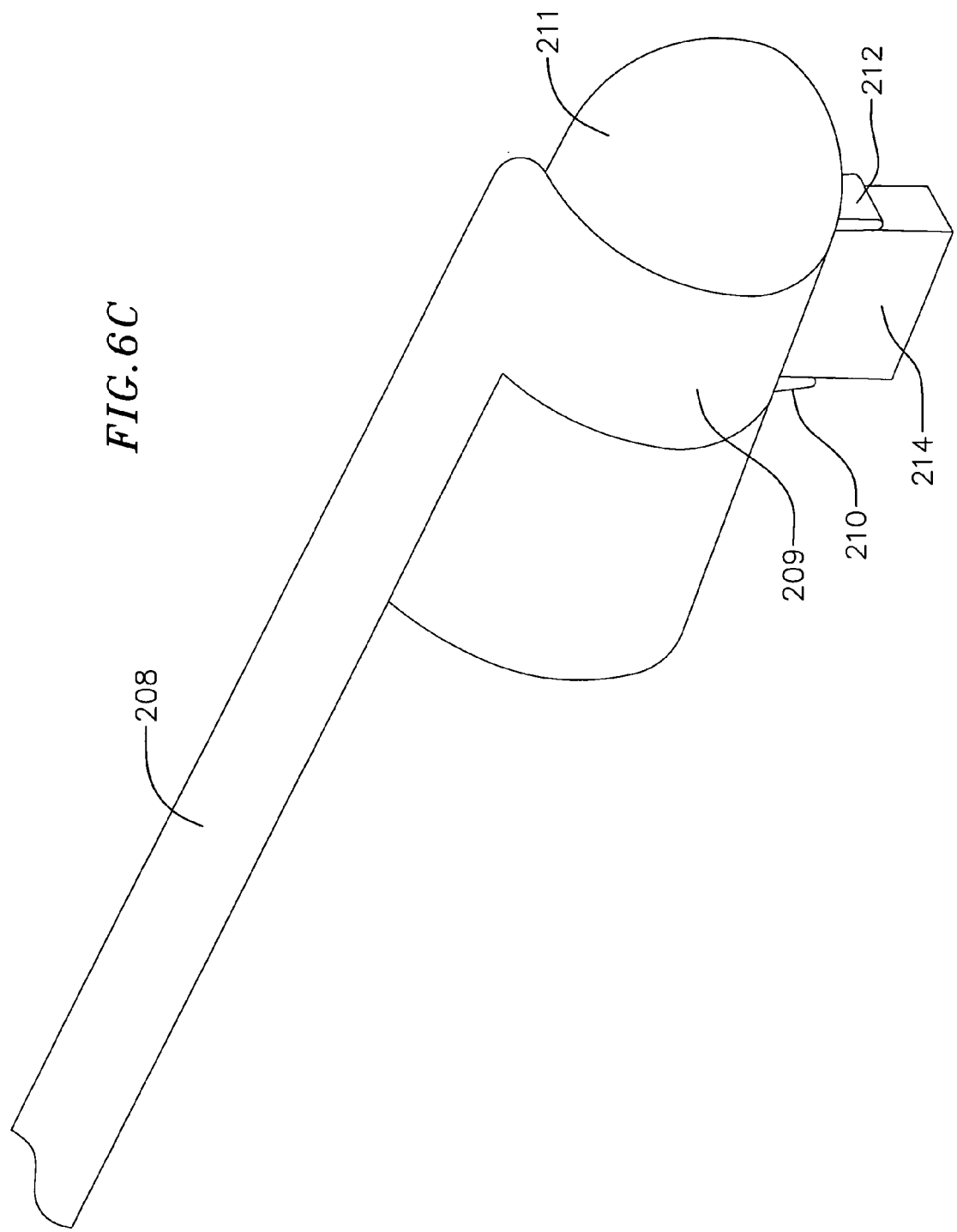

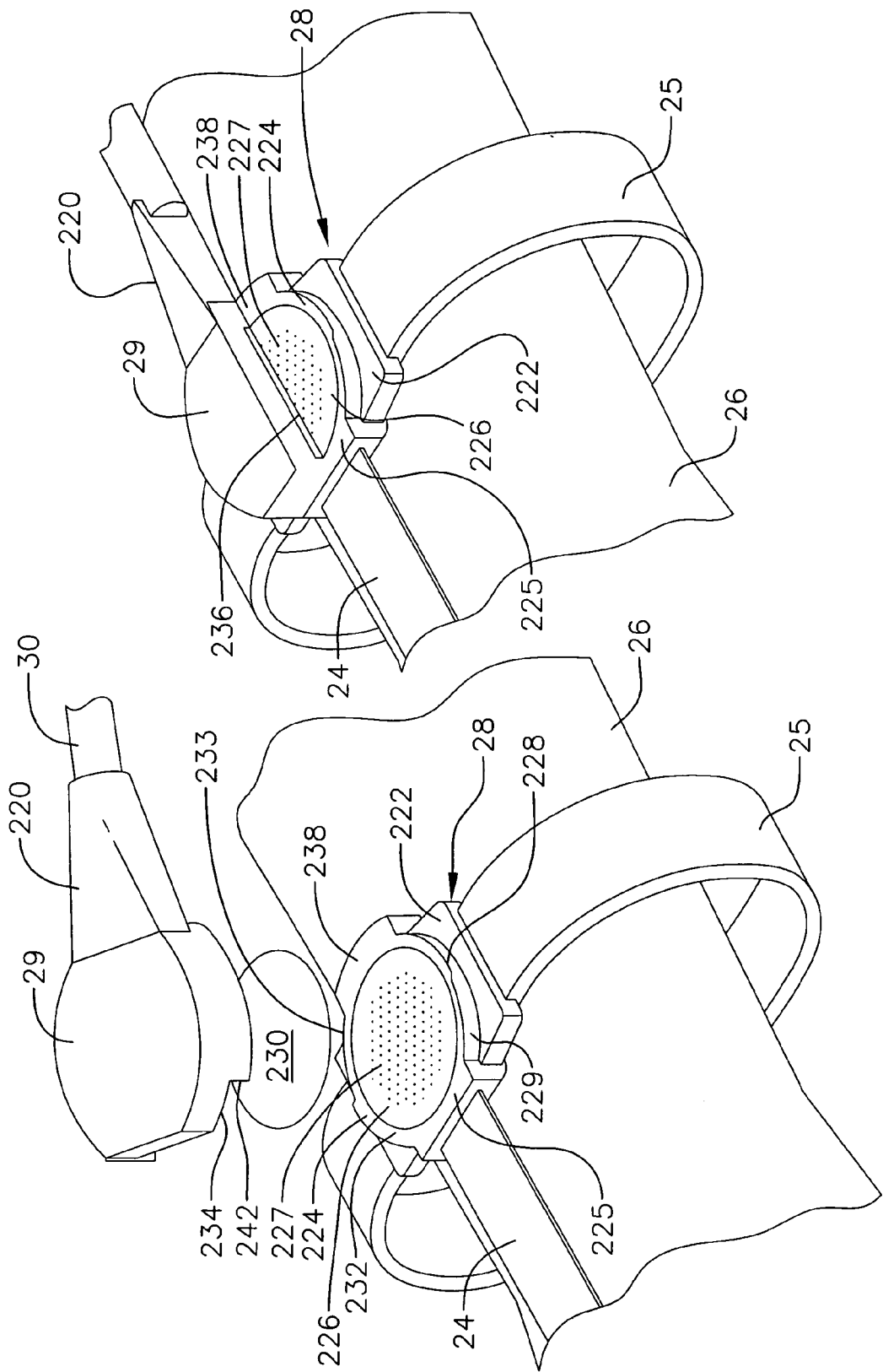

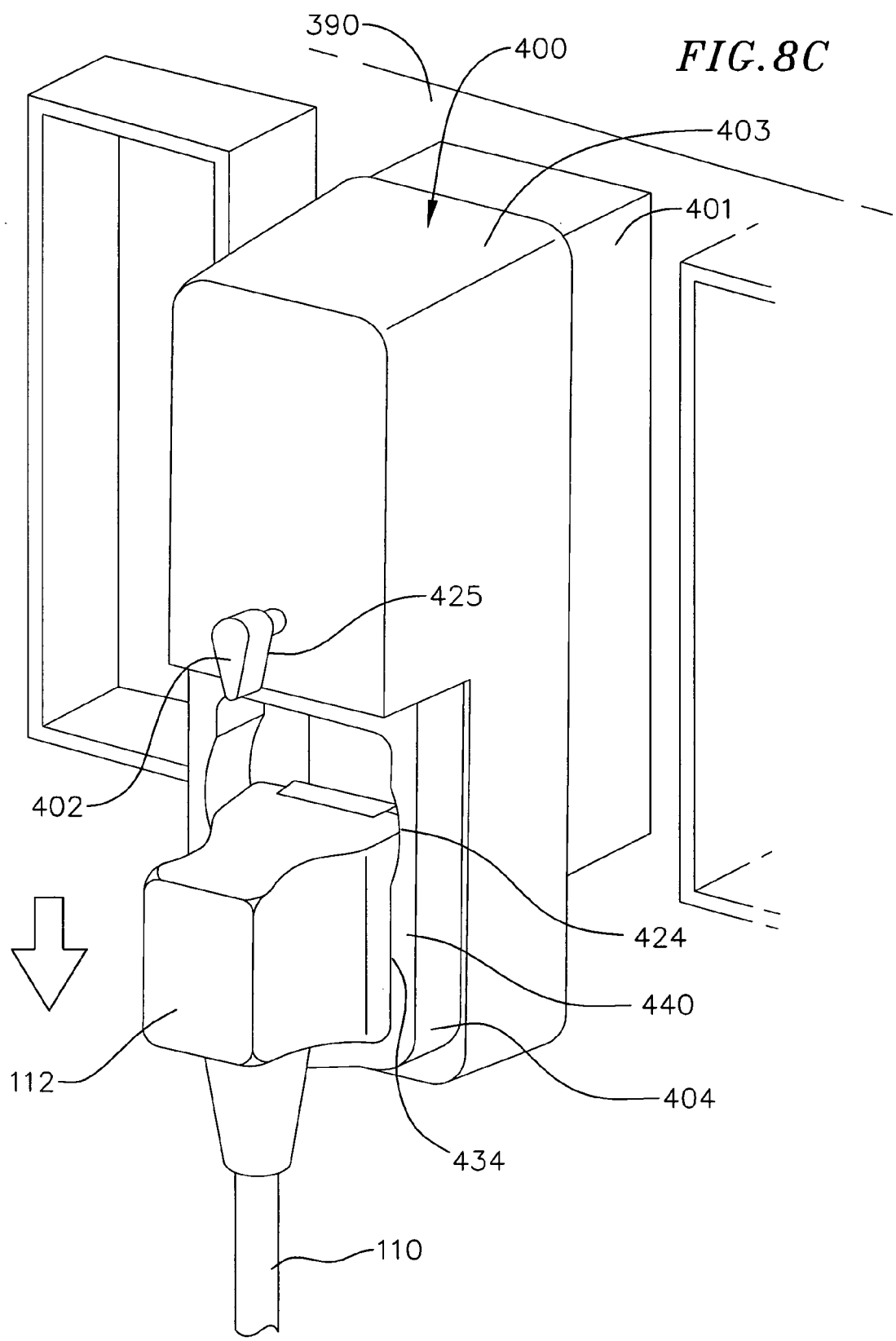

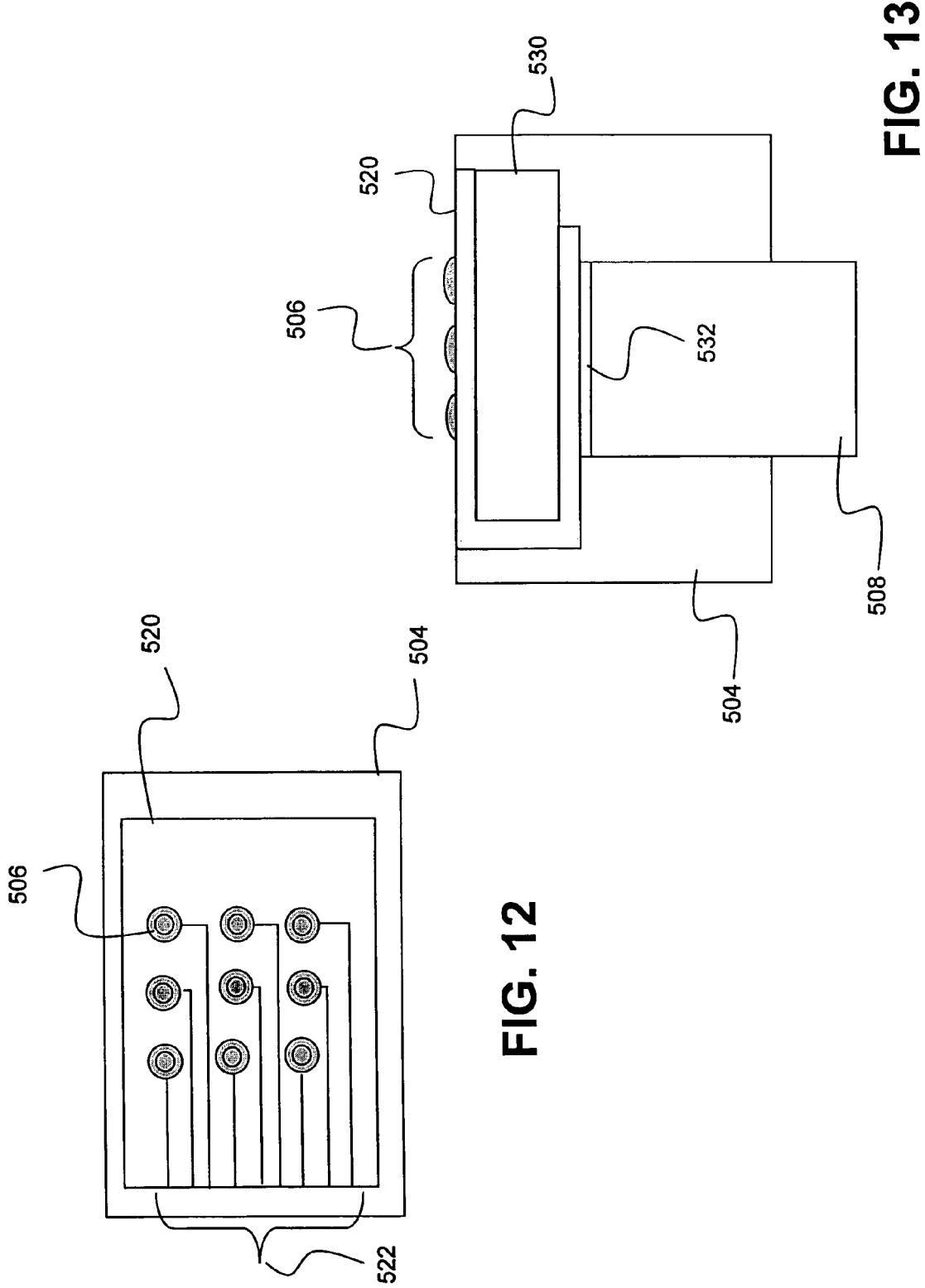

IMMERSIBLE ULTRASOUND PROBE AND CABLE

CROSS REFERENCE TO RELATED APPLICATIONS

This application claims the priority to and the benefit of U.S. Provisional Patent Application No. 60/429,614 entitled "Steam Autoclavable Ultrasound Probe Connector" filed Nov. 27, 2003, the entire content of which is incorporated herein by reference.

FIELD OF THE INVENTION

The present invention is related to ultrasound probe and its connecting cable, and particularly to a finger mounted ultrasound probe, cable and connector for medical ultrasound imaging that can be sterilized through immersion in a disinfecting liquid and/or steam autoclaving.

BACKGROUND

Ultrasound sensors (e.g., transducers) are widely used for diagnosis and medical testing, imaging in invasive procedures, body cavity imaging, use in a cannula, laparascopic procedures and the like. It is often difficult to manipulate, maneuver and position small ultrasound sensors in order to achieve a proper acoustic coupling. In addition, the ultrasound sensors and any connectors attached thereto should be sterilizable.

SUMMARY

In an exemplary embodiment of the present invention, a probe assembly is provided. A sensor assembly is mounted in a housing, which has a finger mountable portion such that the probe can be worn on a finger by a user. The housing includes an inner housing, and an outer housing for holding the inner housing and the sensor assembly. The housing has been sealed such that moisture cannot enter between the inner housing and the outer housing during sterilization of the probe assembly.

In another exemplary embodiment of the present invention, a sterilizable connector is provided. A connector housing has been sealed to prevent moisture from entering it. A multi-wire cable is electrically coupled to a probe at a first end and coupled to the connector housing at a second end. The multi-wire cable has its second end sealed within the connector housing to prevent moisture from entering the sealing between the multi-wire cable and the connector housing. A plurality of electrical contacts are formed on at least one surface of the sterilizable connector. The sterilizable connector can be connected to a mating connector of a medical equipment. The mating connector has a plurality of mating contacts formed thereon for electrical coupling with the electrical contacts of the sterilizable connector. The sterilizable connector can be separated from the mating connector to be sterilized.

In yet another exemplary embodiment of the present invention, a medical ultrasound system is provided. A ultrasound platform can be used to generate, process and display ultrasound images. A probe is used to take ultrasound images. A sterilizable connector includes a connector housing which has been sealed to prevent moisture from entering it. A multi-wire cable is electrically coupled to the probe at a first end and coupled to the connector housing at a second end. The multi-wire cable has its second end sealed with the connector housing to prevent moisture from entering the sealing between the multi-wire cable and the connector housing. A plurality of electrical contacts are formed on at least one surface of the sterilizable connector. A standard connector is used to directly connect to the ultrasound platform. A mating connector can electrically couple the sterilizable connector to the standard connector. The mating connector has a plurality of mating contacts formed thereon for electrical coupling with the electrical contacts of the sterilizable connector. The sterilizable connector can be separated from the standard connector and the mating connector, such that the probe and the sterilizable connector can be sterilized.

BRIEF DESCRIPTION OF THE DRAWINGS

These and other aspects of the invention may be understood by reference to the following detailed description, taken in conjunction with the accompanying drawings, wherein:

FIGS. 2A-2E illustrate first through fifth exemplary embodiments of probe and cable assemblies according to the present invention;

FIG. 3 is a PCB assembly of the fifth exemplary embodiment of the present invention;

FIGS. 4A-4C illustrate a sterilizable connector in exemplary embodiments of the present invention;

FIGS. 5A-5E illustrate finger mounted probes in exemplary embodiments of the present invention;

FIGS. 6A-6C illustrate finger mounted probes in one exemplary embodiment of the present invention;

FIGS. 7A-7B illustrate connection between a wrist connector and a cable connector in an exemplary embodiment of the present invention;

FIGS. 8A-8C illustrate a process of mounting a sterilizable connector to an adapter in an exemplary embodiment of the present invention;

FIG. 12 is a mating surface view of the sterilizable connector of FIG. 11;

FIG. 13 is a cross-sectional view of the sterilizable connector of FIG. 11;

DETAILED DESCRIPTION

Figure 1:
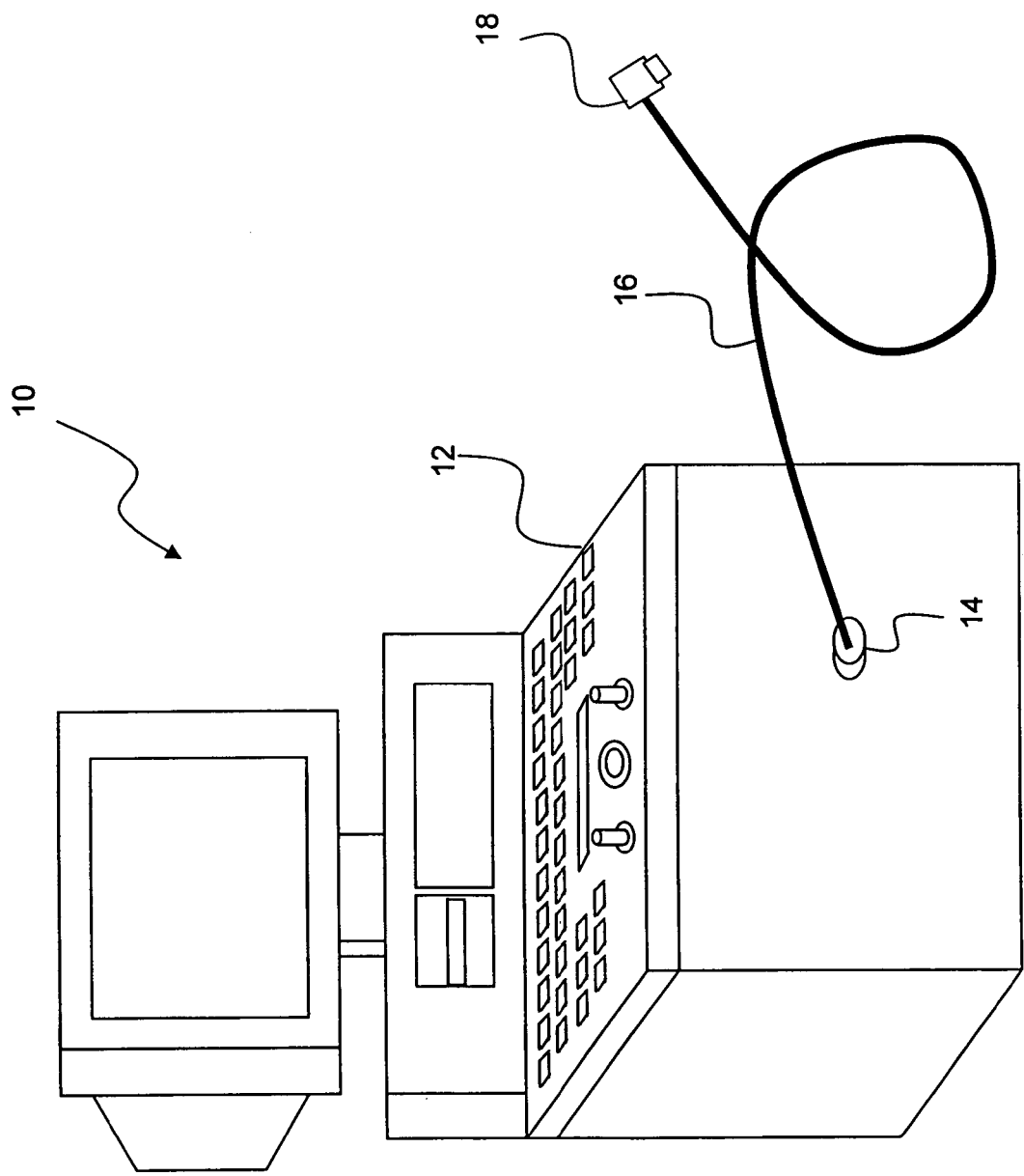
FIG. 1 is a medical ultrasound system, which includes a finger mounted probe and a sterilizable probe connector in an exemplary embodiment according to the present invention.

FIG. 1 is a system diagram of a medical ultrasound system 10 in an exemplary embodiment of the present invention.

The medical ultrasound system 10 includes an ultrasound platform 12, which provides a user (e.g., a medical technician) with capabilities to generate, process and display ultrasound images using a probe (also referred to as a probe head or an autoclavable probe) 18. The probe 18 includes a sensor assembly (e.g., a transducer assembly) for taking ultrasound images. For example, the probe 18 may be a sterilizable finger mounted probe, and may include an array of ultrasound sensors for ultrasound imaging.

The probe 18 is coupled to the platform 12 via a cable 16 and a connector assembly 14. The cable 16 should be a multi-wire cable that can carry multiple signals at the same time. The connector assembly 14 includes a sterilizable connector, which may be a large pin count, low insertion force, steam autoclavable connector suitable for medical ultrasound applications.

The probe 18 may be sterilized, for example, through immersion in a disinfecting liquid and/or steam autoclaving. The sterilizable connector may also be sterilized in a similar manner. The disinfecting liquid, for example, may include Glutaraldehyde (Cidex) and/or Clorohexidine-gluconate solutions. During steam autoclaving, for example, the probe and the attached connector may be exposed to 206.8 Kpa (kilopascal) (or 30 psi (pound per square inch)) steam for 15 minutes.

The connector assembly 14 also includes an adapter assembly. The adapter assembly includes a connector (also referred to as a mating connector) to be mated to the sterilizable connector and a connector (also referred to as a standard connector) to be mated to the ultrasound platform (i.e., a standard connector). The standard connector, for example, can mate to a connector of a standard medical ultrasound system, such that the sterilizable connector of the present invention can be used with conventional medical ultrasound systems. Otherwise, the sterilizable probe attached to the sterilizable connector may not be compatible with existing commercial medical ultrasound systems, thus limiting marketability thereof. The standard connector may be any common ultrasound connector including, but not limited to, DL series of Zero Insertion Force (ZIF) connectors available from ITT Cannon. In other embodiments, the connector assembly 14 may not include an adapter assembly; instead, the sterilizable connector may connect directly with a mating connector on the ultrasound platform 12.

FIGS. 2A-2E illustrate exemplary embodiments of a probe and cable. In each of these exemplary embodiments, the probe is used to provide high frequency sound waves (i.e., ultrasound), which are coupled to an imaging subject across an acoustic seal. The acoustic seal may include a sound conductive gel, which couples the sound waves between the probe and the imaging subject.

While each of FIGS. 2A-2E illustrates an open-ended finger type probe, in practice, the probes can be close-ended or open-nail ended (in which only the finger nail portion of the probe is open ended), and/or any other suitable probes that are sterilizable through immersion and/or steam autoclaving. In one exemplary embodiment, for example, the probes should withstand at least 1,000 cleaning and sterilization cycles without substantial degradation in performance.

Figure 2A:

FIG. 2A illustrates a first exemplary embodiment of a probe and cable assembly 20 in accordance with the present invention. A probe 22 is coupled via a cable 24 to a wrist connector 28 on a cuff mount 25, which can be worn on a wrist of the user. The probe 22, the cable 24, the cuff mount 25 and the wrist connector 28 are immersible in a disinfecting liquid (e.g., Glutaraldehyde (Cidex) and/or Clorohexidine-gluconate solutions) and/or steam autoclavable for sterilization. The probe 22, for example, is a finger mounted probe. The cable 24, for example, may be formed from a flexible planar circuit.

The wrist connector 28 can be detachably connected to an ultrasound platform using a cable 30. The cable 30 has a connector 29 for coupling with the wrist connector 28 and a connector 32 for connecting to the ultrasound platform. Since the cable 30 is detachable from the cuff mount 25, the wrist connector 28, the cable 24, and the probe 22, which together may be referred as an immersible probe assembly, the cable 30 is not necessarily sterilizable, e.g., through immersion or steam autoclaving.

The probe 22 can perhaps be better described in reference to FIG. 5A. The probe 22 has a generally cylindrical finger mount 144, which is shaped for wearing on a finger of the user in much the same manner as a ring. In order to allow different users having different finger sizes to wear a same-sized probe 22, a finger cot 140 that may have varying sizes and thicknesses can be worn over the user's finger first prior to wearing the finger mount 144. The probe 22 also has formed thereon a sensor housing 142 for mounting a sensor assembly therein. Probes in the exemplary embodiments of FIGS. 2C-2E may also have a configuration that is substantially the same as the configuration of probe 22.

In one exemplary embodiment, the sensor assembly, for example, may include an array of 96 sensors (i.e., transducers) having a pitch of about 4 mils (i.e., approximately 101.6 micro meters), an elevation focus of 35 milimeter (mm) radius and an elevation of 6 mm. The sensor assembly may be for operation at 5 mega Hertz (MHz) or 7.5 MHz, or any other suitable frequency. The acoustic frequency may be 6+ MHz with a −6 dB bandwidth greater than 40%. The impedance of the sensor array may be between approximately 400 and approximately 700 ohms over approximately 4.5 to approximately 9 MHz.

Figure 2B:
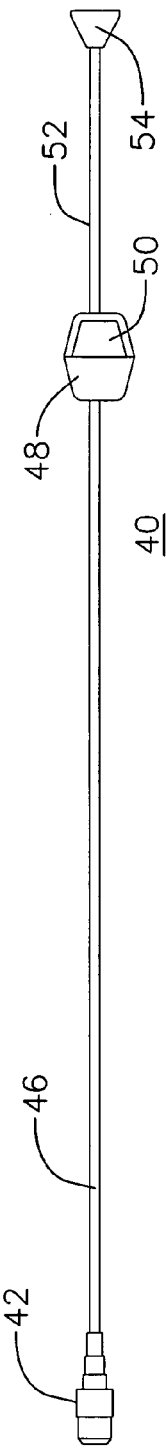
Figure 2C:
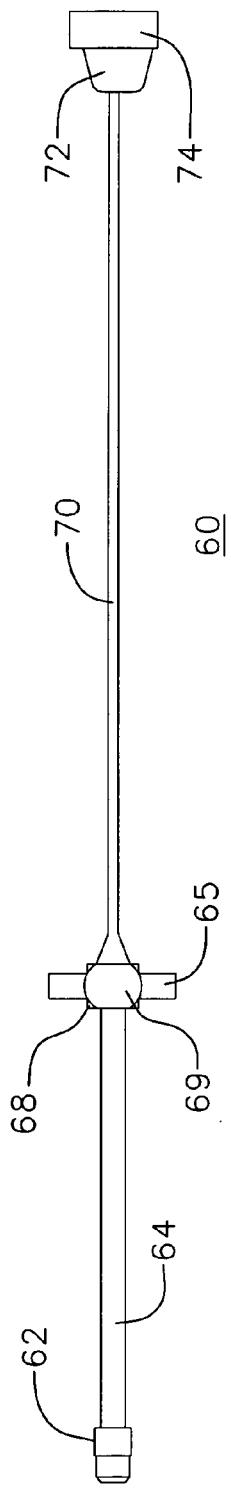
Figure 2D:
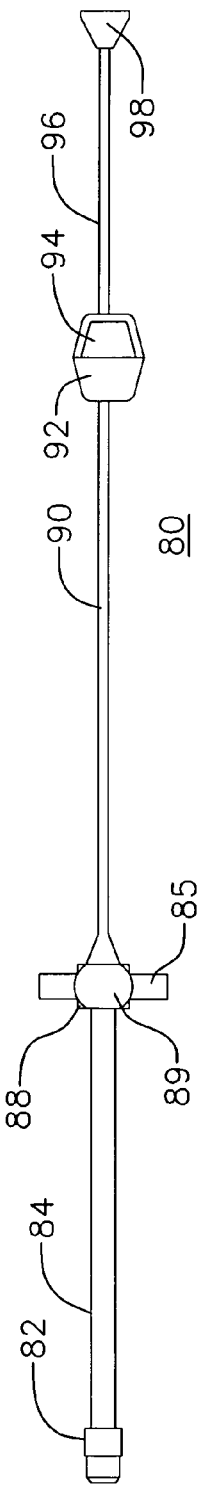

FIG. 6A illustrates a probe 200 that can be used instead of the probe 22 or the probes in FIGS. 2C-2E. The probe 200 has an outer housing 202, which has a hemispherical tip 203 and a generally cylindrical section 204. The hemispherical tip 203 and the generally cylindrical section 204 define an elongated cavity through which a finger of a user can be inserted. The open end of the generally cylindrical section 204 has a circular cross-section whose radius is larger than that of the circular cross-section of the end abutting the hemispherical tip 203.

On the outer surface of the generally cylindrical section 204 is formed thereon a sensor housing 206 for mounting a sensor therein. The sensor housing 206 has a substantially rectangular block shape, and has an opening 207 at the bottom (i.e., side opposite the side attached to the cylindrical section 204) for emitting ultrasound waves, and for sensing the reflected ultrasound waves for imaging. A finger cot 205 having various different sizes and thicknesses may be worn on the finger before wearing the probe 200, such that users having various different finger sizes may use a one-size-fits-all probe.

FIGS. 6B and 6C illustrate, respectively, a cross-sectional view of the probe 200 and the components inside the outer housing 202 of the probe 200. The flexible circuit 208 has attached at the probe end a bow-shaped flexible circuit section 209 that wraps about half way around the inner housing 211. The flexible circuit 208 may also include two overlaid flexible circuits that are substantially parallel to each other. Each of the two overlaid flexible circuits may include the bow-shaped flexible circuit, which together may wrap around the inner housing 211 with a cross-section of an ellipse or a circle.

The inner housing 211 has attached thereto two brackets 210 and 212 for holding the sensor assembly 214. The brackets 210, 212 and the sensor assembly 214 are substantially contained inside the sensor housing 206. The sensor housing 206 has the opening 207 at the bottom for exposing the sensor array of the sensor assembly 214 for ultrasound imaging. The inner and outer housings should be sealed together such that moisture cannot enter between the inner and outer housings during sterilization (e.g., immersion in a disinfecting liquid and/or steam autoclaving). The sensor housing 206 should also be sealed to prevent moisture from entering the housing 200 between the opening 207 and the sensor assembly 214. The sensor housing 206, for example, may be sealed by suitable adhesive and/or through overmolding the assembly.

FIGS. 5A to 6C illustrate finger probes having non-rotated sensor arrays. In other words, the sensor array is pointing straight down, where its surface is substantially parallel to the surface of the finger portion on which the finger probe is mounted. In other embodiments, the sensor array may be constructed so as to face forward or backward by angles of 10 degrees, 20 degrees, and so on. Using a finger probe with a rotated sensor array, portions of a human body can be imaged at a different angle without re-orienting the finger wearing the finger probe.

FIG. 2B illustrates a second exemplary embodiment of a probe and cable assembly 40 in accordance with the present invention. A probe 42 is coupled via a cable 46 to a sterilizable connector 48. The sterilizable connector 48 interfaces with a cable 52 via a connector 50. At the other end of the cable 52 is a connector 54, which may be a standard connector for connecting to a ultrasound medical platform. The probe 42, for example, is a finger mounted probe. The probe 42, the cable 46 and the connector 48 are sterilizable, for example, through immersion in a disinfecting liquid (e.g., Glutaraldehyde (Cidex) and/or Clorohexidine-gluconate solutions) and/or steam autoclaving. The cable 52 and its connectors 50 and 54 can be detached from the sterilizable connector 48, and are not necessarily sterilizable.

The sterilizable connector 48 may be mounted on a belt or at the back of a user such that the user can easily unplug the immersible sub-assembly including the probe 42, the cable 46 and the sterilizable connector 48 from the cable 52, and at the same time not be encumbered by the loose end of the cable 46. The probe 42 may be attached to the cable 46 via a molded finger probe strain reliever such that the electrical connection between the probe 42 and the cable 46 is not damaged through the strain between the probe 42 and the cable 46.

The probe 42 can perhaps be better described in reference to FIG. 5B. The probe 42 has a generally cylindrical finger mount 154, which is shaped for wearing on a finger of the user in much the same manner as a ring. In order to allow different users having different finger sizes to wear a same-sized probe 42, a finger cot 150 that may have varying sizes and thicknesses can be worn over the user's finger first prior to wearing the finger mount 154. The probe 42 also has formed thereon a sensor housing 152 for mounting a sensor assembly therein. Unlike the probe 22 of FIG. 5A, the probe 42 has integrated (e.g., through molding) to the finger mount 154 a strain reliever 156, which is used to relieve strain in the electrical connections between the probe 42 and the cable 46. Similar strain relievers may also be used with the probe 22 and other probes.

FIG. 2C illustrates a third exemplary embodiment of a probe and cable assembly 60 in accordance with the present invention. A probe 62 is coupled via a cable 64 to a wrist connector 68 on a cuff mount 65, which can be worn on a wrist of the user. The probe 62, the cable 64, the cuff mount 65 and the wrist connector 68 are immersible in a disinfecting liquid (e.g., Glutaraldehyde (Cidex) and/or Clorohexidine-gluconate solutions) and/or steam autoclavable for sterilization. The probe 62, for example, is a finger mounted probe. The cable 64, for example, may be formed from a flexible planar circuit.

The wrist connector 68 can be detachably connected to an ultrasound platform using a cable 70. The cable 70 has a connector 69 for coupling with the wrist connector 68 and a connector 72 for connecting to the ultrasound platform through an adapter 74. Since the cable 70 is detachable from the cuff mount 65, the wrist connector 68, the cable 64, and the probe 62, which together may be referred as an immersible probe assembly, the cable 70 is not necessarily sterilizable, e.g., through immersion and/or steam autoclaving. However, as the cable 70 is electrically connected to the ultrasound platform through the adapter 74, the connector 72 is not necessarily a standard ultrasound equipment connector, and can be a steam autoclavable connector. Therefore, the cable 70 and its connectors 69 and 72 may also be sterilizable through immersion in a disinfecting liquid and/or steam autoclaving.

FIG. 2D illustrates a fourth exemplary embodiment of a probe and cable assembly 80 in accordance with the present invention. A probe 82 is coupled via a cable 84 to a wrist connector 88 on a cuff mount 85, which can be worn on a wrist of the user. The probe 82, the cable 84, the cuff mount 85 and the wrist connector 88 are immersible in a disinfecting liquid (e.g., Glutaraldehyde (Cidex) and/or Clorohexidine-gluconate solutions) and/or steam autoclavable for sterilization. The probe 82, for example, is a finger mounted probe. The cable 84, for example, may be formed from a flexible planar circuit.

The wrist connector 88 can be detachably connected to an ultrasound platform through cables 90 and 96. The cable 90 has a connector 89 for coupling with the wrist connector 88 and a connector 92 for connecting to the ultrasound platform through the cable 96. The cable 96 has a connector 98 (e.g., a standard ultrasound equipment connector) for electrically connecting to the ultrasound platform, and a connector 94 for connecting with the connector 92 of the cable 90.

Since the cables 90 and 96 are detachable from the cuff mount 85, the wrist connector 88, the cable 84, and the probe 82, which together may be referred as an immersible probe assembly, the cables 90 and 96 are not necessarily sterilizable, e.g., through immersion and/or steam autoclaving. However, as the cable 90 is electrically connected to the ultrasound platform through the detachable cable 96, the connector 92 is not necessarily a standard ultrasound equipment connector, and can be a steam autoclavable connector. Therefore, the cable 90 and its connectors 89 and 92 may also be sterilizable through immersion in a disinfecting liquid and/or steam autoclaving.

FIG. 2E illustrates a fifth exemplary embodiment of probe and cable assembly 100 in accordance with the present invention. The probe and cable assembly 100 is similar in configuration as the probe and cable assembly 60 of FIG. 2C, except that the probe and cable assembly 100 does not have a wrist connector and it is made of a single immersible probe assembly whose components cannot be easily detached from each other. Also, a probe 102 is shown without a removable finger cot for inserting a finger fittably into the probe. In addition, the probe 102 shows a sensor housing 104 for holding a sensor assembly, which is attached thereto. In practice, all the probes of FIGS. 2A-2D each have a similar sensor housing.

The probe 102 is coupled via a cable 106 to a printed circuit board (PCB) assembly 108. The PCB assembly 108 is connected to a sterilizable connector 112 via a cable 110. Since the PCB assembly 108 is not readily detachable from the cable 110 in the fifth exemplary embodiment, all of the probe 102, the cable 106, the PCB assembly 108, the cable 110 and the connector 112 are immersible in a disinfecting liquid (e.g., Glutaraldehyde (Cidex) and/or Clorohexidine-gluconate solutions) and/or steam autoclavable for sterilization. The cable 106, for example, may be formed from a flexible planar circuit. Since the connector 112 is not a standard ultrasound equipment connector, it interfaces with an ultrasound platform via an adapter (or alternatively, via another cable).

FIGS. 5C-5E show the probe 102 of the probe and cable assembly 100 of FIG. 2E. The probe 102 may be substantially the same as the probe 22 of FIG. 5A, and may also be used in the exemplary embodiments of FIGS. 2A, 2C and 2D. The probe 102 has a generally cylindrical outer housing 103 and the sensor housing 104 attached thereto. A sensor assembly 117 is mounted inside the sensor housing 104. The sensor assembly 117 has a generally rectangular cross-section, and has at its bottom surface a sensor array 119 (i.e., transducer array) for ultrasound imaging. The sensor housing 104 has a generally rectangular opening for allowing the sensor array 119 to be exposed.

Disposed within the outer housing 103 is an inner housing 111. The inner housing 111 also has a generally cylindrical shape, and fits substantially tightly within the outer housing 103. The inner housing 111 has attached thereto brackets 116 and 118 for holding the sensor assembly 117. The brackets 116 and 118 as well as the sensor assembly 117 fit substantially within the sensor housing 104.

The inner and outer housings should be sealed together such that moisture cannot enter between the inner and outer housings during sterilization (e.g., immersion in a disinfecting liquid and/or steam autoclaving). Further, the sensor housing 104 should be sealed such that moisture does not enter into the housing between the sensor assembly 117 and the periphery of the opening at the bottom. The probes 22 and 42 of FIGS. 2A, 5A, 2B, 5B, respectively, should be sealed in a similar manner.

As shown in FIG. 5E, the flexible circuit 106 includes two flat flexible circuits 112 and 114 that are substantially parallel to each other. The flexible circuit 112 is overlaid on top of the flexible circuit 114 through most of the length of the flexible circuit 106. One end of the flexible circuit 106 is terminated to a PCB 120 as shown in FIG. 3. The other end of the flexible circuit 106 has attached thereto a pair of bow-shaped flexible circuit sections 113 and 115. The two flexible circuit sections 113 and 115 together form an elliptical section that fits between the inner housing 111 and the outer housing 103. The flexible circuit section 113 at its top end is electrically connected to the flexible circuit 114, whereas the flexible circuit section 115 at its top end is electrically connected to the flexible circuit 112. Both the flexible circuit sections 113 and 115 terminate at the sensor assembly 117 at their respective bottom ends.

In other embodiments, the probe inner/outer housing may have various different shapes suitable for mounting on a finger. For example, the inner and/or outer housing may not encircle the finger completely, but may only partially envelope the finger with an opening at the top. The inner and/or outer housing may also envelope the end of the finger similar to the probe 200 of FIGS. 6A-6C, except for an opening near its front edge to expose only a finger nail portion (or a part thereof) of the finger.

FIG. 3 illustrates the PCB assembly 108 of FIG. 2E. The PCB assembly 108 includes a PCB 120 (shown in phantom lines) encased in a PCB housing 126. The PCB assembly 108 may also be referred to as a wrist adapter, and the PCB housing 126 may be referred to as a wrist adapter over mold. The cable 106 is electrically coupled to the PCB 120 at terminations 122 (shown in phantom lines), whereas the cable 110 is electrically coupled to the PCB 120 at terminations 124 (shown in phantom lines). This way, electrical connections can be made between the cables 106 and 110. The PCB housing 126 also has strain relievers 127 and 128 formed thereon for engaging the ends of the cables 106 and 110, respectively, so as to relieve strain to the electrical connections between the PCB 120 and the cables 106 and 110.

FIG. 4A is a perspective view of the sterilizable connector 112 at the other end of the cable 110. The sterilizable connector 112 can be sterilized through steam autoclaving. In other embodiments, the sterilizable connector 112 may be sterilized through immersion, for example, in a disinfecting liquid. As can bee seen in FIGS. 4A-C, the sterilizable connector 112 has a connector housing 130 for fixedly holding a flexible circuit 131 and a flexible circuit support 132. The connector housing 130 also has formed thereon a strain reliever 135 for relieving strain in electrical connections between the flexible circuit 131 and the cable 110.

The flexible circuit support 132 is formed of two support pieces that are substantially perpendicular to one another. The first (substantially square shaped) support piece is parallel to the interface surface of the connector 112. The second (substantially rectangular) support piece is mounted on the first support piece on the other side of the interface surface. The support pieces are attached together through plug-and-hole type connections, pins, or any other suitable fastening mechanism.

The flexible circuit 131 may be made of a number of connected folded portions for wrapping around the first support piece and covering most of the second support piece on both sides. For example, the flexible circuit 131 includes end portions 170 (e.g., overlaid on each side of the second support piece), a rear surface portion 176 (overlaid on the rear surface of the first support piece), intermediate portions 172 and 174 (e.g., overlaid on the back surface portion 176), an upper edge portion 178 and a front surface portion 180 (which forms the interface surface of the connector 112). The back surface portion 176 of the flexible circuit between the two support pieces may have holes formed thereon to allow the two support pieces to be attached together therethrough.

The connector housing 130 has a generally cubical shape with one end bigger than the other end. Between the bigger and smaller ends are concave sections 129 that are formed for ease of holding by a user for plugging/unplugging the connector to an adapter. The strain reliever 135 extends downward from a bottom surface of the connector housing 130.

The bigger end (i.e., an interface surface) of the connector housing 130 has exposed thereon the front surface portion 180 of the flexible circuit 131. On the front surface portion 180 has formed thereon multiple contacts 133 for electrically interfacing with the contacts on an adapter. In one exemplary embodiment, there are approximately 200 contacts on the flexible circuit 131. In other exemplary embodiments the number of contacts may range from 200 to 500. In still other exemplary embodiments, less than 200 or more than 500 contacts may be used. The front surface portion 180 and the contacts 133 formed thereon are surrounded by a frame 139 that encircle the periphery of the interface surface of the connector housing 130 except for an opening 137 at the top.

Left and right edges of the frame 139 are formed as convex protrusions 134, each of which has a shape of a tip of a circle formed by cutting the circle with a vertical chord. Inner edges 136 of the frame 139 that correspond to the convex protrusions 134 also have a similar shape. An upper edge of the front surface portion 180 is adjacent to the opening 137 of the frame 139 at the top of the connector housing 130. However, a lower edge of the front surface portion 180 is farther away from the bottom inner edge of the frame 139, thereby leaving an exposed area 138 of the interface surface that is not overlaid by the front surface portion 180. The exposed area 138 has a general shape of an upside down pentagon (i.e., with the tip pointing down), which has been elongated in a horizontal direction.

FIGS. 7A and 7B illustrate the wrist connector 28 and the interaction between the wrist connector 28 and the cable connector 29. The wrist connector 28 can be mounted on a human arm 26 using the cuff mount 25. The cuff mount 25 is hingedly coupled to the wrist connector 28 such that it can be opened or closed with respect to the arm 26. In other embodiments, the wrist connector 28 may be mounted on the human arm 26 using any other suitable mechanism. Attached to the cable connector 29 is a strain reliever 220 for relieving the strain in electrical connections between the cable connector 29 and the cable 30.

The wrist connector 28 has a generally rectangular lower portion 222 coupled to the cuff mount 25 and a generally circular upper portion 224 that protrudes upward from the lower portion 222. The wrist connector 29 has formed thereon a contact surface 226 having a plurality of contacts 227. On the periphery of the generally circular portion 224 are non-engaging portions 229 and 233 that are located at substantially 180 degrees of each other. A curved engaging protrusion 228 is formed on the periphery portion adjacent to the non-engaging portion 229. In addition, a curved engaging protrusion 232 is formed on the periphery portion adjacent to the non-engaging portion 233. The curved engaging protrusions 228 and 232 are also located at substantially 180 degrees of each other. Rotation stops 225 and 238 are also formed on the periphery of the generally circular portion 224. The rotation stop 225 is aligned with the flexible circuit 24. The rotation stop 238 is located at substantially 180 degrees from the rotation stop 225.

The cable connector 29 has formed thereon a curved peripheral wall 242 attached adjacently to the strain reliever 220. The connector 29 has also formed thereon another curved peripheral wall (not shown) located substantially 180 degrees from the curved peripheral wall 242. Adjacent to the peripheral wall 242 is a non-walled portion 234. A similar non-walled portion (not shown) is located substantially 180 degrees from the non-walled portion 234. On the inside periphery of a portion of the curved peripheral wall 242 is formed a curved protrusion (not shown). In addition, there is another curved protrusion located on said another curved peripheral wall at substantially 180 degrees from the curved protrusion of the peripheral wall 242.

The cable connector 29 has also formed thereon a contact surface 236 having a plurality of electrical contacts that are aligned with the electrical contacts 227 of the wrist connector during normal operation. An anisotropic contact pad (i.e., z-axis conductive pad) 230 is placed between the contact surfaces 226 and 236 such that as the contact surfaces are brought close together, multiple thin parallel wires between the electrical contacts in the contact pad 230 are deformed (see FIG. 15, for example), and electrical connections are made between corresponding electrical contacts.

When the cable connector 29 is initially mounted on the wrist connector 28, it is at an angle where the cable is not aligned with the arm 26 of the user. This way, the curved protrusions on the cable connector 29 are aligned with the non-engaging portions 229 and 233, respectively, of the wrist connector 28, and the curved engaging protrusions 228 and 232 on the wrist connector 28, respectively, are aligned with the portions of the curved peripheral walls of the cable connector 29 that do not have the curved protrusions.

Upon initial mounting, the cable connector is rotated to lock with the wrist connector 28. The rotation of the cable connector 29, for example, may be stopped by the rotation stops 225 and/or 228. The curved engaging protrusions 228 and 232 on the wrist connector 28 and/or the curved protrusions on the cable connector 29 may be slanted (e.g., spiraling) such that the cable connector is brought closer to the wrist connector as the curved protrusions engage and slide with respect to one another. In other embodiments, any other suitable locking mechanism may be used to lock the cable connector 29 to the wrist connector 28. The wrist connector 28 is immersible in a disinfecting liquid and/or steam autoclavable such that it can be sterilized. Steam autoclavable/immersible connectors in other exemplary embodiments are discussed below in reference to FIGS. 11-15.

FIGS. 8A-8C, 9 and 10A-10B illustrate an adapter 400 that interfaces between the steam autoclavable connector 112 and a ultrasound platform 390. The adapter 400 includes an adapter housing 403, on which a standard ultrasound equipment connector 413 is mounted for mating with an equipment connector 401 on the ultrasound platform 390.

In one exemplary embodiment, the standard ultrasound equipment connector 413 (and therefore the adapter 400) is mated with the equipment connector 401 using a toggle latch assembly 402. The toggle latch assembly 402 is a standard component on existing ultrasound connectors, and includes a main shaft 422 that goes through the entire body of the connector (through the adapter 402 in this case). At one end is a teardrop shaped handle that may be referred to as a toggle latch 425. At the other end is a short shaft (not shown) that goes through the main shaft 422 at substantially a right angle, thereby forming a cross-shape "key" at the end.

In operation, the adapter 400 (including the standard ultrasound equipment connector 413) is pushed into its mate (the equipment connector 401) and the cross-shaped key fits into a slot in the equipment connector 401. As the main shaft 422 is rotated using the toggle latch 425, the key engages the equipment connector 401, thereby bringing the adapter 400 and the mating connector 401 closer together. At approximately 90 degrees of rotation, the key locks into place. To disengage the two mating connectors, the process is simply reversed.

The toggle latch assembly described above is known to those skilled in the art. Those skilled in the art would also appreciate that the short shaft for forming the "key" may be replaced by other shaped components, and the selection of the "key" is based on the type of ultrasound platform used.

In addition, any other mating/locking mechanism known to those skilled in the art may be used instead of the toggle latch assembly to mate the adapter to the ultrasound platform as long as such mating/locking mechanism is supported by the ultrasound platform.

The adapter 400 also includes an alignment frame 404, an adapter probe mate 406, a backing plate 405 and a shuttle rear plate 411. The adapter probe mate 406 has a plurality of contacts 410 formed thereon. These contacts 410 correspond to and are for forming electrical connections with the contacts 133 of the sterilizable connector 112 via an anisotropic contact pad 408 (i.e., z-axis conductive pad). The contacts 410 are electrically connected to an adapter flexible circuit 420 that are electrically connected through the connector 413 to the equipment connector 401.

The alignment frame 404 includes a wider opening 424 and a narrower opening 434. The probe mate 406 also has a corresponding wider region 427 and a narrower region 429. The sides of the wider opening 424 and the wider region 427 are shaped to match the convex protrusions 134 of the sterilizable connector 112. Therefore, the sterilizable connector 112 can initially be mated via the contact pad 408 with the wider region 427 of the adapter probe mate 406 through the wider opening 424. The narrower opening 434 has formed along its side peripheries vertical protrusions 440.

The adapter probe mate 406 is mounted on the shuttle rear plate 411 through an opening 442 on the adapter housing 403. The adapter probe mate 406 and the shuttle rear plate 411 are slidably mounted on the adapter housing 403 such that they can together slide up and down.

Figure 8A:
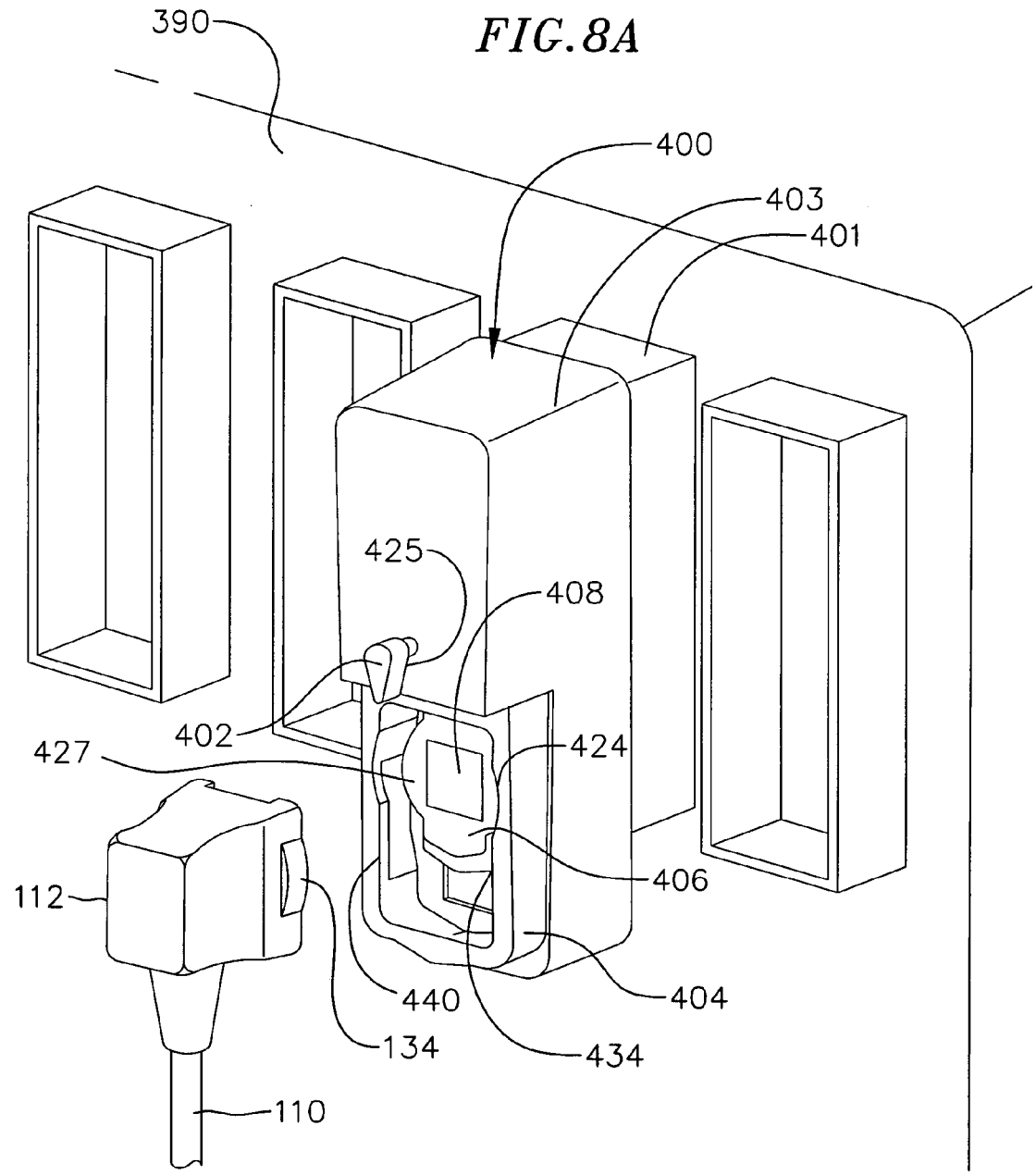
Figure 8B:
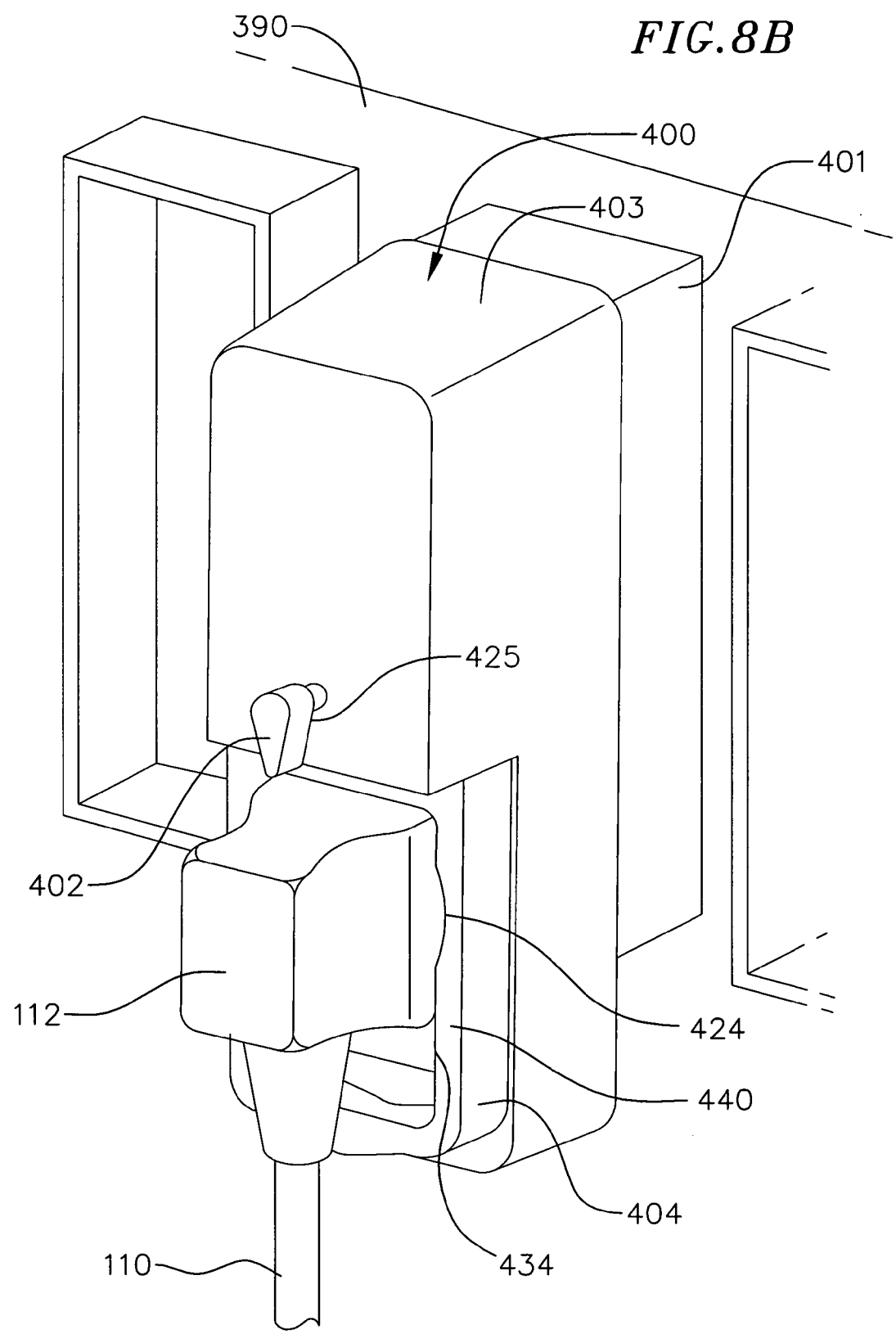
Figure 9:
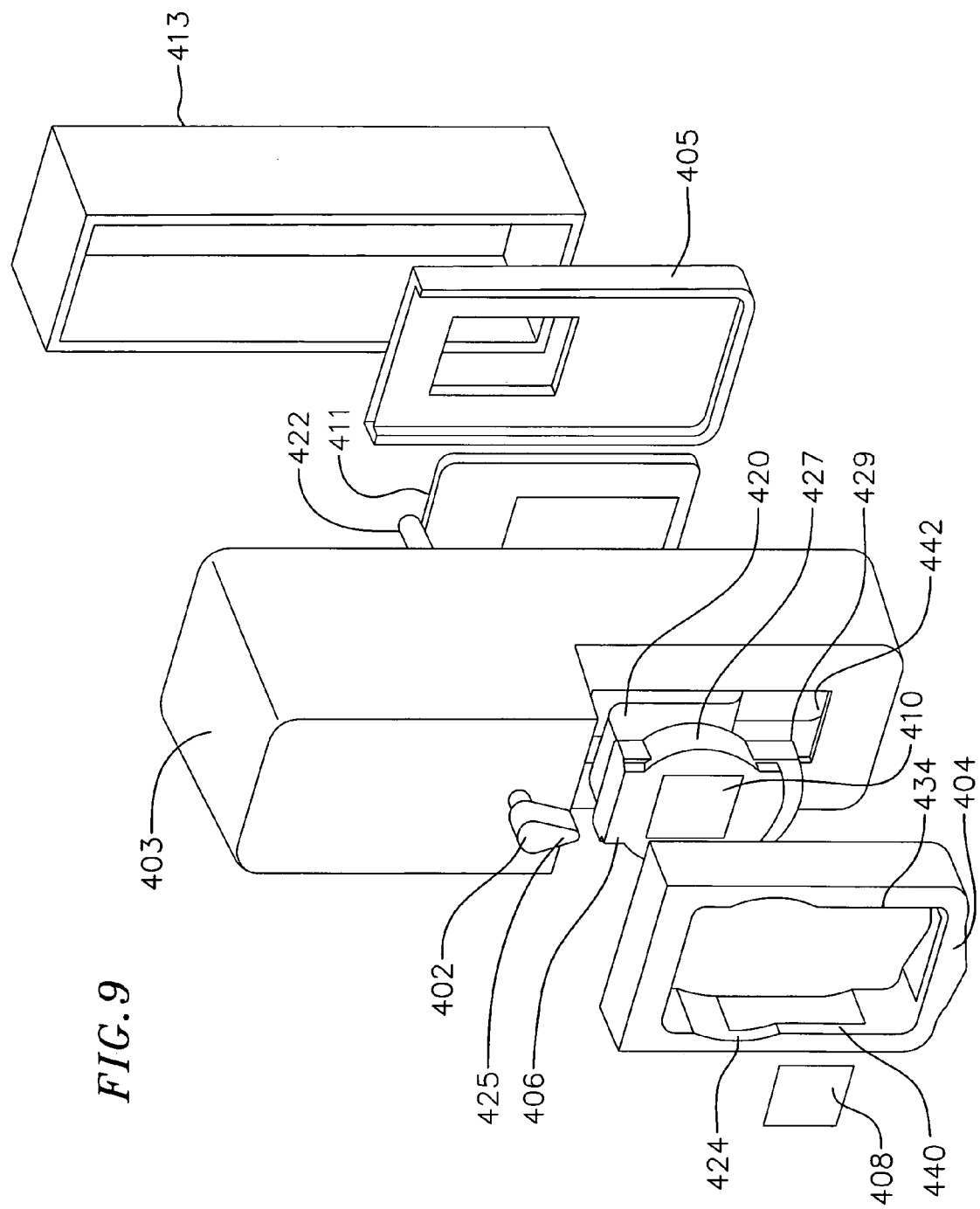
FIG. 9 is an exploded view of the adapter of FIGS. 8A-8C.
Figure 10:
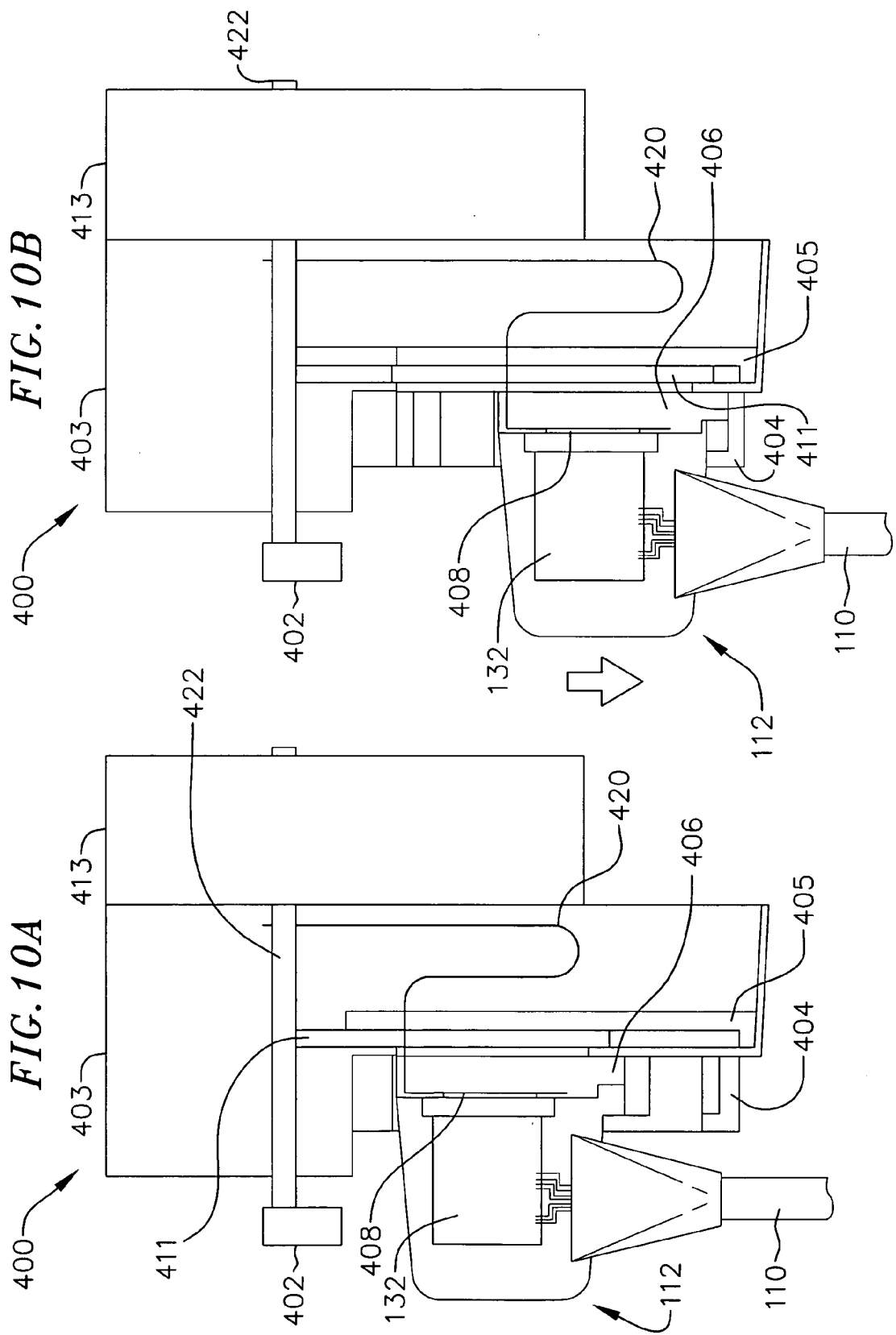
FIGS. 10A-10B illustrate a cross sectional side view of the process of mounting the sterilizable connector to the adapter of FIGS. 8A-8C.

As can be seen in FIG. 8A, the sterilizable connector 112 is first aligned with the wider opening 424 of the alignment frame 404 and the wider region 427 of the adapter probe mate 406. Then, as seen in FIGS. 8B and 10A, the sterilizable connector 112 is mated with the adapter probe mate 406 via the contact pad 408 through the wider opening 424. The adapter 400 at this point is already mated with the equipment connector 401 using the toggle latch assembly 402.

As can be seen in FIGS. 8C and 10B, after the contact is made, the sterilizable connector 112 is slid down with respect to the adapter housing 403. Along with the sterilizable connector, the adapter probe mate 406 and the shuttle rear plate 411 are also slid down. The alignment frame 404, however, remains stationary with respect to the adapter housing 403. Since the narrower opening 434 has formed along its side peripheries vertical protrusions 440, as the sterilizable connector 112 is slid down, the convex protrusions 134 are pinned under the vertical protrusions 440, such that the sterilizable connector 112 is tightly coupled to the adapter probe mate 406.

As the contact surfaces are brought close together, multiple thin parallel wires between the electrical contacts in the contact pad 408 are deformed (see FIG. 15, for example), and electrical connections are made between corresponding electrical contacts. This way, the contact pad 408 electrically connects the contacts 133 with the contacts 410.

Figure 11:
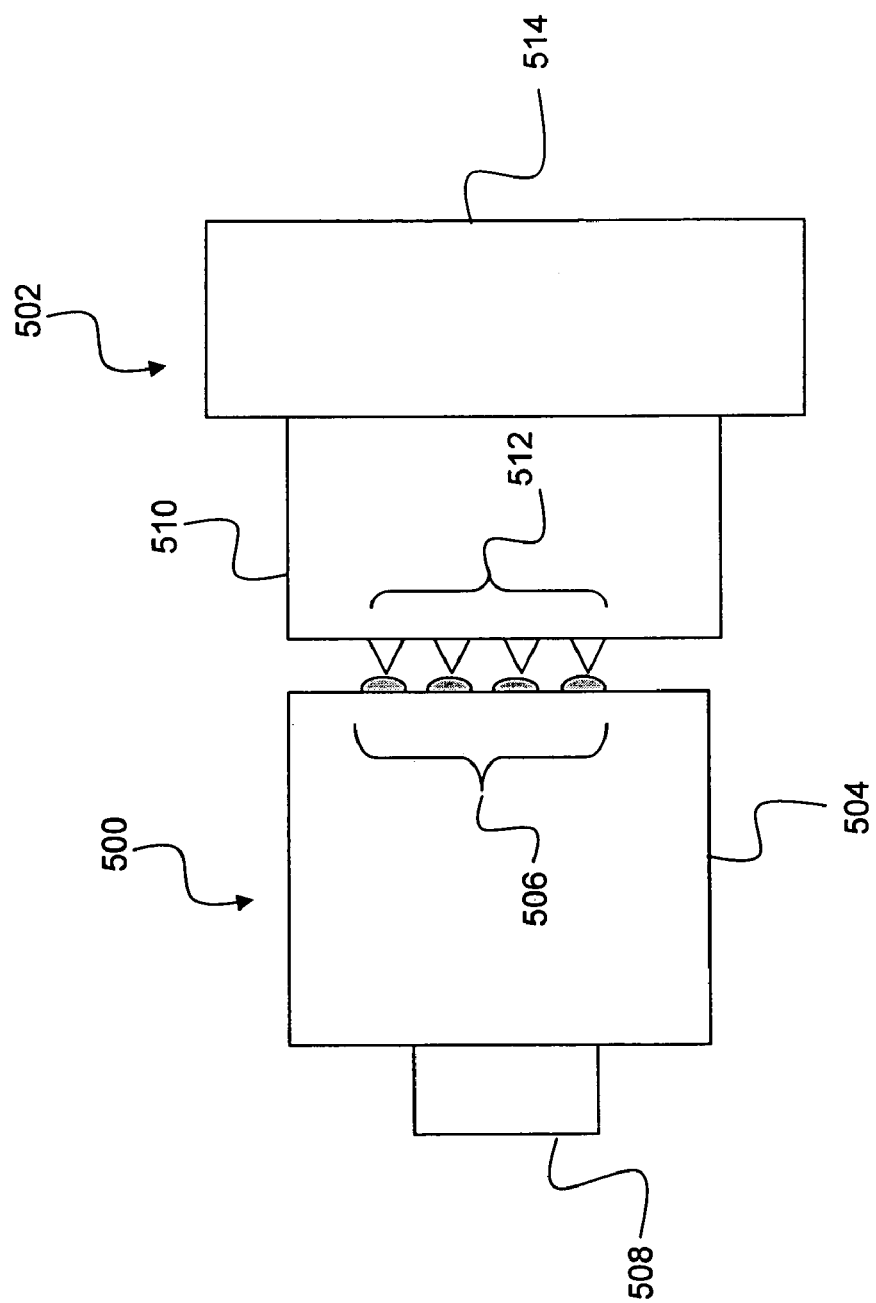
FIG. 11 illustrates a connector assembly in an exemplary embodiment according to the present invention, where a sterilizable connector electrically interfaces with a standard ultrasound equipment connector via a mating connector.

FIG. 11 illustrates a connector assembly in an exemplary embodiment according to the present invention, where a sterilizable connector 500 interfaces with an adapter assembly 502, which includes a standard ultrasound equipment connector 514 and a mating connector 510. The connector assembly of FIG. 11, for example, can be used as the connector assembly 14 of FIG. 1. Since the adapter assembly 502 can be coupled and de-coupled with the sterilizable connector 500, it may not need to be sterilizable. The sterilizable connector 500 interfaces with the standard ultrasound equipment connector 514 via the mating connector 510. The mating connector 510 may also be referred to as an adapter.

As discussed above, in other embodiments, the mating connector 510 may be mounted on the ultrasound platform instead of interfacing with the standard ultrasound equipment connector 514. In these embodiments, the sterilizable connector 500 can be connected directly to the ultrasound platform.

The sterilizable connector 500 includes multiple electrical contacts 506 mounted thereon to electrically interface with mating contacts 512 on the mating connector 510. The sterilizable connector 500 includes a flexible printed wiring board that is molded into a probe connector housing 504. This provides for an inexpensive and rugged design that, due to its integrated one-piece design, is autoclavable (i.e., steam sterilizable). A cable 508 (also referred to as a probe connector cable or a probe cable) should also be sealed at one end to and within the probe connector housing 504 so that steam sterilization does not damage the sterilizable connector 500 by introducing moisture into it. The cable 508 should be a multi-wire cable that can conduct various different signals between the ultrasound platform 12 and the probe 18.

When electrical connections are made between the sterilizable connector 500 and the adapter assembly 502, they are held in place, for example, using a locking mechanism known to those skilled in the art. The locking mechanism may include rotate-and-lock mechanism, slide-and-lock mechanism and/or any other suitable locking mechanism for tightly coupling two electrical contact surfaces together, and is used to ensure good electrical contacts between the electrical contacts 506 and the mating contacts 512.

FIG. 12 illustrates a mating surface view of the sterilizable connector 500. As seen in FIG. 12, the sterilizable connector includes a printed wiring board (i.e., flexible circuit or printed wiring substrate) 520 molded in the probe connector housing 504. The printed wiring board 520 has formed thereon a number of wires 522 (e.g., wire traces) for carrying various different electrical signals and/or to provide power and ground. The printed wires 522, for example, are electrically coupled to the electrical contacts 506.

As seen in FIG. 13, the sterilizable connector 500 includes the printed wiring board 520, the cable 508, and a backing 530 that are molded together in the probe connector housing 504. The sterilizable connector 500 also includes contacts 532 for connecting the printed wiring board 520 to the cable 508.

The materials used to construct the sterilizable connector 500 should be selected such that a seamless, hermetic bond between the components can be formed. Further, a chemical bond may also be formed between the components. Such construction should avoid even the smallest of cracks or seams in which pathogens can survive. The materials should also be selected such that the probe connector housing 504 will survive repeated autoclaving cycles without losing its hermetic seal or mechanical integrity. The probe connector housing 504, for example, may be made of polymer.

All external material (for all the probes and connectors of the present invention) that may come into contact with human body should be FDA certified. Those skilled in the art would know how to select FDA certified materials that meet requirements for fabricating the probes and the sterilizable connectors of the present invention.

The electrical contacts 506 in the exemplary embodiment may also be referred to as gold contacts or gold bumps when it is formed by plating a relatively thick gold layer over printed wiring (e.g., copper wiring) 522 of the flexible printed wiring board 520 (i.e., flexible circuit). The gold contacts are selected for the exemplary embodiment because of at least the following properties. Pure gold is a soft, highly conductive and low reactivity metal. The high conductivity and softness provide for an excellent low contact force electrical connection. The low reactivity should ensure that the contact surface will not be adversely affected by harsh environmental conditions (such as encountered during autoclaving).

As discussed above, the autoclavable connector is realized through the use of gold plated contacts on a unitized molded connector in the described exemplary embodiment. Another notable feature of the described exemplary embodiment is the properties of the backing 530 for the flexible printed wiring board 520. The backing 530 should be selected to have appropriate compliance to allow motion between the mating (or contact) surfaces (i.e., electrical contacts 506 and the mating contacts 512) as the connection is made. In addition, the backing 530 should provide a spring force to keep the two surfaces in contact. Further, a relative motion between the mating surfaces provides a mechanism for removing contaminants between the mating surfaces, thereby allowing a reliable electrical connection between the electrical contacts and the mating contacts.

Figure 14:
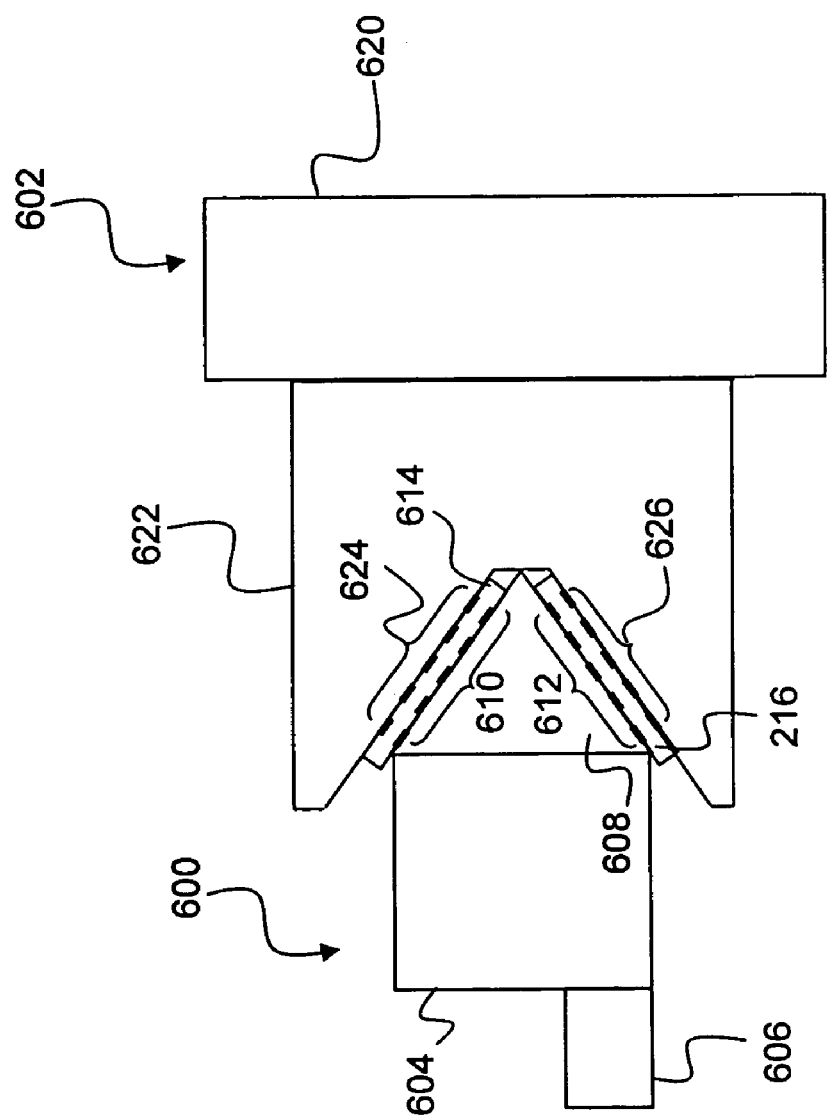
FIG. 14 illustrates a connector assembly in another exemplary embodiment according to the present invention, where a sterilizable connector electrically interfaces with a standard ultrasound equipment connector via a mating connector.

FIG. 14 illustrates a connector assembly in another exemplary embodiment according to the present invention, where a sterilizable connector 600 interfaces with an adapter assembly 202, which includes a mating connector 622 and a standard ultrasound equipment connector (also referred to as a standard connector) 620. A cable 606 (which may be multi-wire) is connected to connector sections 604 and 608 of the sterilizable connector 600. In other embodiments, the connector sections 604 and 608 may be a single integrated component. The connector assembly of FIG. 14, for example, may be used as the connector assembly 14 coupled to the ultrasound platform 12 of FIG. 1.

As discussed above, in other embodiments, the mating connector 622 may be mounted on the ultrasound platform instead of interfacing with the standard ultrasound equipment connector 620. In these embodiments, the sterilizable connector 600 can be connected directly to the ultrasound platform.

The connector assembly of FIG. 14 may be said to incorporate a "contact pad" design, in which anisotropic conducting contact pads (i.e., z-axis conductive pads) 614, 616 (also referred to as contact pads) are used, respectively, to make the electrical connection between sterilizable connector's contacts 610, 612 and mating connector's contacts 624, 626. Using the "contact pad" design, the connector contacts can be made out of a hard, electrically conductive material and yet have reliable electrical connection using relatively low forces to mate the connectors. Use of the "contact pad" design, therefore should provide a significant increase in connector lifetime. In addition, using removable contact pads may simplify cleaning of the adapter assembly 602 since the contact pads 614 and 616 may be disposable. Further, the contact pads 614 and 616 are deformable, and should be able to provide the contaminant removing mechanical motion and spring force.

When electrical connections are made between the sterilizable connector 600 and the adapter assembly 602, they are held in place, for example, using a locking mechanism known to those skilled in the art. The locking mechanism may include rotate-and-lock mechanism, slide-and-lock mechanism and/or any other suitable locking mechanism for tightly coupling two electrical contact surfaces together, and is used to ensure good electrical contacts between the contacts 610 and 624 using the contact pad 614, and between the contacts 612 and 626 using the contact pad 616.

Figure 15:
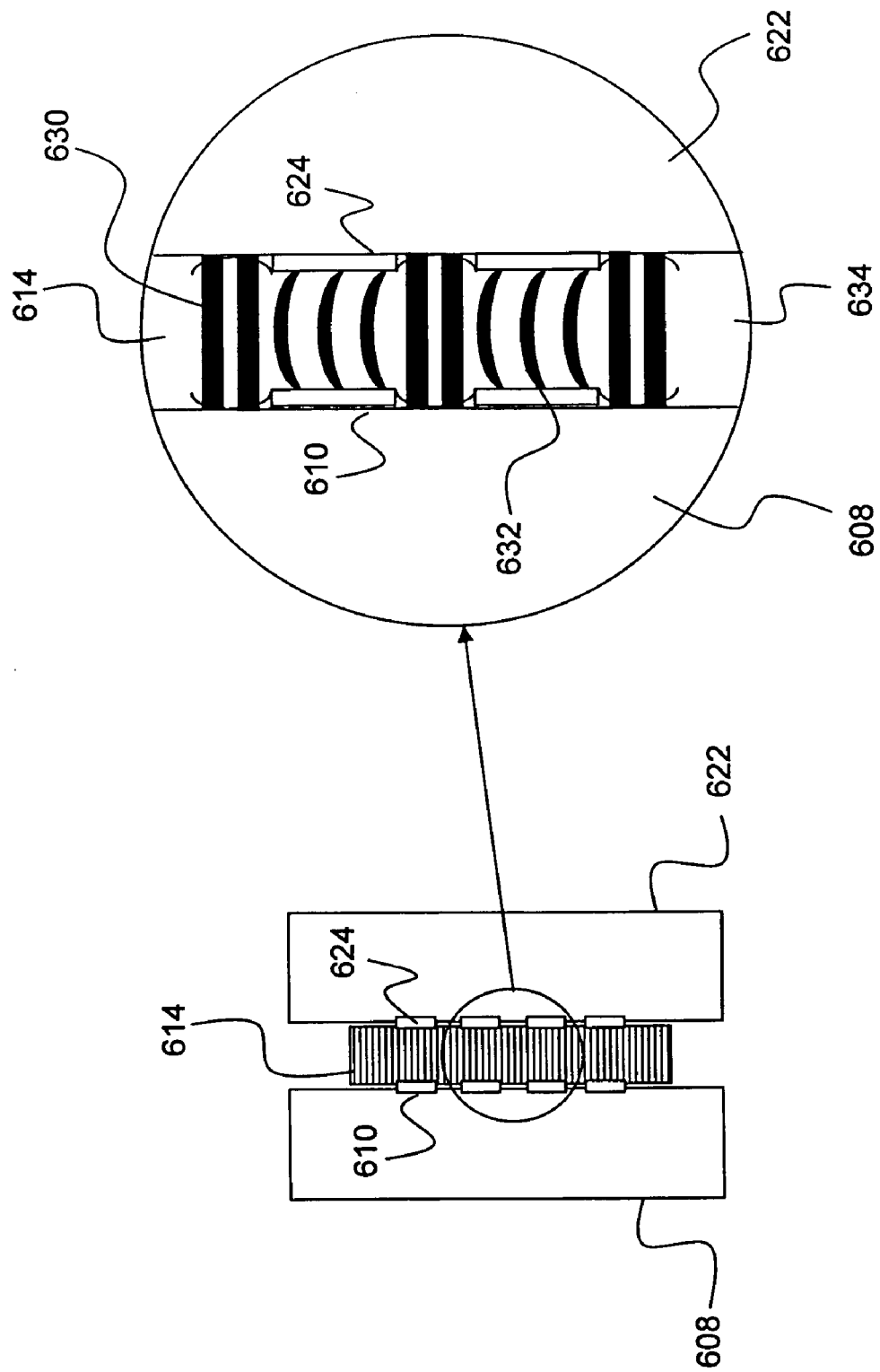
FIG. 15 illustrates an anisotropic conducting pad that interfaces between the sterilizable connector and mating connector of FIG. 14.

FIG. 15 illustrates the anisotropic conducting contact pad 614 that interfaces between the sterilizable connector 608 and the mating connector 622. The contact pad 616 has substantially the same configuration and usage as the contact pad 614. As seen in FIG. 15, the contact pad 614 includes multiple thin parallel wires 630 that are imbedded in a compliant polymer matrix 634. The polymer matrix 634 serves to insulate each wire as well as to provide suitable compliant mechanical support. The resultant structure should conduct electrical current in only one direction, hence the thin parallel wires 630 function as anisotropic conductors.

Due to their anisotropic conductive nature, the contact pads 614 and 616 can be used to connect multiple sets of contact surfaces without shorting adjacent conductive contacts. In other words, the polymer matrix 634 prevents the embedded wires from touching each other so as to prevent shorts between them. Further, the compression due to mating forces causes the connecting wires to deform to deformed wires 632. This motion serves to remove surface contaminants, thereby permitting a reliable electrical contact. The polymer matrix 634 should be selected such that it provides the necessary spring force to keep the deformed wires 632 in constant contact with the electrical contact surfaces.

The anisotropic conducting contact pads (or contact pads) are typically used to provide low-insertion-force, multi-contact connections between high value and/or fragile electronic components and a mating connector. The advantage of this connector system is the ability to make extremely dense, large quantity, reliable, very low force electrical connections. The anisotropic conducting contact pads may be disposable. The general use of the anisotropic conducting contact pads and the selection of suitable polymer matrix are known to those skilled in the art.

In this exemplary embodiment, the use of the contact pads allows the use of a hard contact surface between the two mating connectors. Hard contact surfaces reduce the scratching and pitting in the contacts seen in traditional gold contact designs. Such pitting may provide a safe haven for pathological agents. These agents could be chemical in nature and hence not be removed by standard cleaning methods, even though autoclaving would render them sterile. Though physical contact between the connector and the body or its fluids would be extremely unlikely, such chemicals, through normal handling, could be transferred to and contaminate other parts of the probe which may then be placed in bodily contact.

The 'V' shape of the sterilizable connector 608 serves to self-center the contact surfaces 610 and 612 (i.e., electrical contacts) to the contact surfaces 624 and 626 (i.e., mating contacts) during mating as well as to provide lateral as well as normal forces to the contact pads 614 and 616. The latter is suitable to help with the necessary wire-to-contact-surface wiping action suitable for removing surface contaminants.

The sterilizable connector 600 should have a unitized molded assembly. The materials used to construct the sterilizable connector 600 should be selected such that a seamless, hermetic bond between the components can be formed. Further, a chemical bond between the components may also be formed. Such construction should avoid even the smallest of cracks or seams in which pathogens can survive. The material for the connector sections 604 and 608 should be selected such that they will survive repeated autoclaving cycles without losing their hermetic seal or mechanical integrity. The connector sections 604 and 608, for example, may be made of polymer. All external material that may come into contact with human body should be FDA certified. Those skilled in the art would know how to select FDA certified materials that meet requirements for fabricating the autoclavable connector of the present invention.

It will be appreciated by those of ordinary skill in the art that the invention can be embodied in other specific forms without departing from the spirit or essential character hereof. The present description is therefore considered in all respects to be illustrative and not restrictive. The scope of the invention is indicated by the appended claims, and all changes that come within the meaning and range of equivalents thereof are intended to be embraced therein.

For example, even though the present invention has been described herein in reference to medical ultrasound systems, it is broadly applicable to any medical or other systems that require use of portable sensor assemblies and/or sterilization of one or more connectors.

We claim:

1. A sterilizable connector comprising:
    a connector housing which has been sealed to prevent moisture from entering it;
    a flexible planar circuit which is electrically coupled to a probe at a first end and coupled to the connector housing at a second end, said flexible planar circuit having its second end sealed with the connector housing to prevent moisture from entering the sealing between the flexible planar circuit and the connector housing; and
    a plurality of electrical contacts formed on at least one surface of the sterilizable connector and on the flexible planar circuit,
    wherein the sterilizable connector can be connected to a mating connector of a medical equipment while the sterilizable connector remains sealed, said mating connector having a plurality of mating contacts formed thereon for electrical coupling with the electrical contacts of the sterilizable connector, and
    wherein the sterilizable connector can be separated from the mating connector to be sterilized.

2. The sterilizable connector of claim 1, wherein the medical equipment comprises an ultrasound platform.

3. A sterilizable connector comprising:
    a connector housing which has been sealed to prevent moisture from entering it;
    a multi-wire cable which is electrically coupled to a probe at a first end and coupled to the connector housing at a second end, said multi-wire cable having its second end sealed with the connector housing to prevent moisture from entering the sealing between the multi-wire cable and the connector housing;
    a plurality of electrical contacts formed on at least one surface of the sterilizable connector; and
    a flexible circuit board and a backing, wherein the flexible circuit board is at least partially wrapped around said backing, and the backing provides a spring force to keep the electrical contacts in contact with the mating contacts,
    wherein the sterilizable connector can be connected to a mating connector of a medical equipment while the sterilizable connector remains sealed, said mating connector having a plurality of mating contacts formed thereon for electrical coupling with the electrical contacts of the sterilizable connector, and
    wherein the sterilizable connector can be separated from the mating connector to be sterilized.

4. The sterilizable connector of claim 3, wherein the flexible circuit board includes a plurality of wires formed thereon and the electrical contacts are formed by plating a gold layer over the wires.

5. The sterilizable connector of claim 3, wherein the flexible circuit board is molded to the connector housing so that the sterilizable connector comprises a unitized molded connector.

6. The sterilizable connector of claim 3, wherein the multi-wire cable comprises a flexible planar circuit.

7. A sterilizable connector comprising:
    a connector housing which has been sealed to prevent moisture from entering it;
    a multi-wire cable which is electrically coupled to a probe at a first end and coupled to the connector housing at a second end, said multi-wire cable having its second end sealed with the connector housing to prevent moisture from entering the sealing between the multi-wire cable and the connector housing; and
    a plurality of electrical contacts formed on at least one surface of the sterilizable connector,
    wherein the sterilizable connector can be connected to a mating connector of a medical equipment, said mating connector having a plurality of mating contacts formed thereon for electrical coupling with the electrical contacts of the sterilizable connector,
    wherein the sterilizable connector can be separated from the mating connector to be sterilized, and
    wherein an anisotropic conducting contact pad is disposed between the sterilizable connector and the mating connector.

8. The connector assembly of claim 7, wherein the anisotropic conducting contact pad comprises a polymer matrix and a plurality of parallel wires embedded in the polymer matrix.

9. The connector assembly of claim 8, wherein the wires between each pair of electrical and mating contacts are deformed upon mating between the sterilizable connector and the mating connector.

10. The sterilizable connector of claim 7, wherein the multi-wire cable comprises a flexible planar circuit.

11. The sterilizable connector of claim 10, wherein the at least one surface of the sterilizable connector on which the plurality of electrical contacts are formed, is on the flexible planar circuit.

12. A sterilizable connector comprising:
    a connector housing which has been sealed to prevent moisture from entering it;
    a multi-wire cable which is electrically coupled to a probe at a first end and coupled to the connector housing at a second end, said multi-wire cable having its second end sealed with the connector housing to prevent moisture from entering the sealing between the multi-wire cable and the connector housing; and
    a plurality of electrical contacts formed on at least one surface of the sterilizable connector,
    wherein the sterilizable connector can be connected to a mating connector of a medical equipment, said mating connector having a plurality of mating contacts formed thereon for electrical coupling with the electrical contacts of the sterilizable connector,
    wherein the sterilizable connector can be separated from the mating connector to be sterilized, and
    wherein mating surfaces between the sterilizable connector and the mating connector is V-shaped, wherein the electrical contacts make electrical connection with the mating contacts on each of the two surfaces of the V-shaped mating surfaces.

13. The sterilizable connector of claim 12, wherein an anisotropic conducting contact pad is disposed on each mating surface between the sterilizable connector and the mating connector when the connectors are mated so as to form electrical connection.

14. The sterilizable connector of claim 13, wherein each anisotropic conducting contact pad comprises a polymer matrix and a plurality of parallel wires embedded in the polymer matrix.

15. The sterilizable connector of claim 14, wherein the wires between each pair of electrical and mating contacts are deformed upon mating between the sterilizable connector and the mating connector.

16. The sterilizable connector of claim 12, wherein the V-shaped mating surfaces provide self-centering during mating between the sterilizable connector and the mating connector.

17. The sterilizable connector of claim 12, wherein the multi-wire cable comprises a flexible circuit. connector.

18. A connector assembly comprising:
   a sterilizable connector comprising:
      a connector housing which has been sealed to prevent moisture from entering it;
      a multi-wire cable which is electrically coupled to a probe at a first end and coupled to the connector housing at a second end, said multi-wire cable having its second end sealed with the connector housing to prevent moisture from entering the sealing between the multi-wire cable and the connector housing; and
      a plurality of electrical contacts formed on at least one surface of the sterilizable connector;
   a standard connector for connecting directly to a standard medical equipment connector of a medical equipment;
   a mating connector for electrically coupling the sterilizable connector to the standard connector while the sterilizable connector remains sealed, said mating connector having a plurality of mating contacts formed thereon for electrical coupling with the electrical contacts of the sterilizable connector,
   wherein the sterilizable connector can be separated from the standard connector and the mating connector to be sterilized.

19. The connector assembly of claim 18, wherein the medical equipment comprises an ultrasound platform.

20. The connector assembly of claim 18, wherein the sterilizable connector further comprises a flexible circuit board and a backing, wherein the flexible circuit board is at least partially wrapped around said backing, and the backing provides a spring force to keep the electrical contacts in contact with the mating contacts.

21. The connector assembly of claim 20, wherein the flexible circuit board includes a plurality of wires formed thereon and the electrical contacts are formed by plating a gold layer over the wires.

22. The connector assembly of claim 20, wherein the flexible circuit board is molded to the connector housing so that the sterilizable connector comprises a unitized molded connector.

23. The connector assembly of claim 18, wherein a relative motion between the electrical contacts and the mating contacts provide a mechanism for removing contaminants between the contacts, thereby allowing a reliable electrical connection.

24. The connector assembly of claim 18, wherein the multi-wire cable comprises a flexible planar circuit.

25. The connector assembly of claim 24, wherein the at least one surface of the sterilizable connector on which the plurality of electrical contacts are formed, is on the flexible planar circuit.

26. A medical ultrasound system comprising:
   an ultrasound platform that can be used to generate, process and display ultrasound images;
   a probe for taking ultrasound images;
   a sterilizable connector comprising:
      a connector housing which has been sealed to prevent moisture from entering it;
      a flexible planar circuit which is electrically coupled to the probe at a first end and coupled to the connector housing at a second end, said flexible planar circuit having its second end sealed with the connector housing to prevent moisture from entering the sealing between the flexible planar circuit and the connector housing; and
      a plurality of electrical contacts formed on at least one surface of the sterilizable connector and on the flexible planar circuit;
   a standard connector for connecting directly to the ultrasound platform;
   a mating connector for electrically coupling the sterilizable connector to the standard connector while the sterilizable connector remains sealed, said mating connector having a plurality of mating contacts formed thereon for electrical coupling with the electrical contacts of the sterilizable connector,
   wherein the sterilizable connector can be separated from the standard connector and the mating connector, such that the probe and the sterilizable connector can be sterilized.

27. The system of claim 26, wherein the sterilization is through one selected from a group consisting of immersion in a disinfecting liquid and steam autoclaving.

28. The system of claim 26, wherein the probe is a sterilizable finger mounted probe.

29. The system of claim 28, wherein the finger mounted probe includes a sensor array that is rotated with respect to a portion of a finger on which the finger mounted probe is mounted.

* * * * *